(12) United States Patent
Bissantz et al.

(10) Patent No.: US 7,893,062 B2
(45) Date of Patent: Feb. 22, 2011

(54) PYRROLIDINE DERIVATIVES AS DUAL NK1/NK3 RECEPTOR ANTAGONISTS

(75) Inventors: Caterina Bissantz, Village-Neuf (FR); Torsten Hoffmann, Weil am Rhein (DE); Philippe Jablonski, Steinbrunn-le-Haut (FR); Henner Knust, Rheinfelden (DE); Matthias Nettekoven, Grenzach-Wyhlen (DE); Hasane Ratni, Habsheim (FR); Xihan Wu, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 488 days.

(21) Appl. No.: 12/102,121

(22) Filed: Apr. 14, 2008

(65) Prior Publication Data
US 2008/0275021 A1  Nov. 6, 2008

(30) Foreign Application Priority Data
Apr. 20, 2007 (EP) .................................. 07106666

(51) Int. Cl.
A61K 31/4015 (2006.01)
A61K 31/5377 (2006.01)
C07D 207/04 (2006.01)
C07D 413/02 (2006.01)

(52) U.S. Cl. .................... 514/235.5; 544/111; 544/141; 544/358; 544/372; 548/530; 514/231.5; 514/252.13; 514/423

(58) Field of Classification Search ................ 544/111, 544/141, 358, 372; 548/530; 514/231.5, 514/235.5, 252.13, 423
See application file for complete search history.

(56) References Cited

U.S. PATENT DOCUMENTS

| 4,143,061 A | 3/1979 | Kubo et al. |
| 5,972,938 A | 10/1999 | Rupniak et al. |
| 2006/0020011 A1 | 1/2006 | Wu et al. |

FOREIGN PATENT DOCUMENTS

| DE | 2659404 | 7/1977 |
| EP | 1192952 | 4/2002 |
| WO | WO 95/16679 | 6/1995 |
| WO | WO 95/18124 | 7/1995 |
| WO | WO 95/23798 | 9/1995 |
| WO | WO 02/079134 | 10/2002 |
| WO | WO 2005/002577 | 1/2005 |
| WO | WO 2006/013050 | 2/2006 |
| WO | WO 2007/011162 | 1/2007 |

OTHER PUBLICATIONS

Kamali et al., Current Opinion in Investigational Drugs (2001) 2(7) pp. 950-956.
Giardina et al., Exp. Opinion Ther. Patents (2000) 10(6) pp. 939-960.
Barker, R., Neurosci. Res. (1996) vol. 7, pp. 187-214.
Longmore et al., Can. J. Phys. (1997) vol. 75 pp. 612-621.
Kramer et al., Science (1998) vol. 281 pp. 1640-1645.
Maggi, et al., Auton. Pharmacol. vol. 13, pp. 23-93 (1993).
Navari et al., The New England Journal of Medicine vol. 340 No. 3, pp. 190-195 (1999).
Fujima et al., Tetrahedron Asymmetry (2003) vol. 14(10) pp. 1385-1391.
Alajarin et al., J. Med. Chem. (1995) vol. 38(15) pp. 2830-2841.
Takahata et al., J. Org. Chem. (1989) vol. 54(20) pp. 4812-4822.
Young, J. et al, *Bioorganic & Med. Chem. Letters*, 17(19): 5310-5315 (2007).

Primary Examiner—Golam M Shameem
(74) Attorney, Agent, or Firm—George W. Johnston; Patricia S. Rocha-Tramaloni; Kimberly J. Prior

(57) ABSTRACT

The invention relates to pyrrolidine derivatives of formula

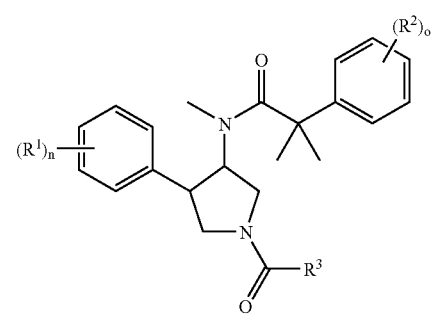

wherein
$R^1$,
$R^2$,
$R^3$,
n, and o are defined in the specification and to pharmaceutically active acid-addition salts thereof. Compounds of formula I have a high affinity simultaneously to both the NK1 and the NK3 receptors (dual NK1/NK3 receptor antagonists), useful in the treatment of schizophrenia.

15 Claims, No Drawings

PYRROLIDINE DERIVATIVES AS DUAL NK1/NK3 RECEPTOR ANTAGONISTS

PRIORITY TO RELATED APPLICATION(S)

This application claims the benefit of European Patent Application No. 07106666.6, filed Apr. 20, 2007, which is hereby incorporated by reference in its entirety.

BACKGROUND OF THE INVENTION

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs*, 2001, 2(7), 950-956 and *Psychiatric Disorders Study* 4, *Schizophrenia*, June 2003, Decision Recources, Inc., Waltham, Mass.). The proposed drug SR 142,801 has been shown in a phase II trial as active on positive symptoms of schizophrenia, such as altered behaviour, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 and *Current Opinion in Investigational Drugs*, 2001, 2(7), 950-956 956 and *Psychiatric Disorders Study* 4, *Schizophrenia*, June 2003, Decision Recources, Inc., Waltham, Mass.).

In addition, EP 1 192 952 describes a pharmaceutical composition containing a combination of a NK3 receptor antagonist and a CNS penetrant NK1 receptor antagonist for the treatment of depression and anxiety.

It has been found that the combination of the antidepressant, mood enhancing properties of NK1 receptor antagonism and the antipsychotic symptoms of NK3 receptor antagonism are suitable to treat both positive and negative symptoms in schizophrenia.

This advantage may be realized in the administration of an ideal drug against schizophrenia.

They have been described as active at the NK1 receptor for the treatment of diseases related to this receptor, such as inflammatory conditions including migraine, rheumatoid arthritis, asthma, and inflammatory bowel disease as well as mediation of the emetic reflex and the modulation of central nervous system (CNS) disorders such as Parkinson's disease, anxiety, pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases.

The neurokinin-1 receptor antagonists are further useful for the treatment of motion sickness, for treatment induced vomiting or for the treatment of psychoimmunologic or psychosomatic disorders, see *Neurosci. Res.*, 1996, 7, 187-214, *Can. J. Phys.*, 1997, 75, 612-621, *Science*, 1998, 281, 1640-1645, *Auton. Pharmacol.*, 13, 23-93, 1993, WO 95/16679, WO 95/18124 and WO 95/23798, *The New England Journal of Medicine*, Vol. 340, No. 3 190-195, 1999, U.S. Pat. No. 5,972,938.

SUMMARY OF THE INVENTION

The invention provides pyrrolidine derivatives of formula I

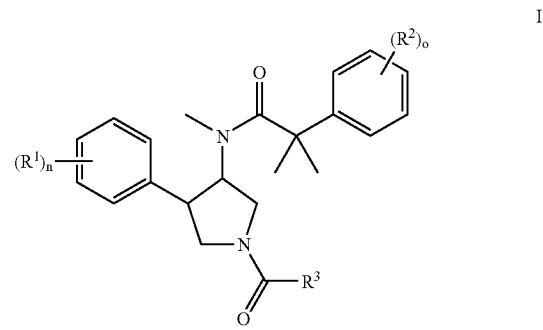

wherein
R$^1$ is hydrogen, halogen or lower alkyl;
R$^2$ is hydrogen, halogen, lower alkoxy or lower alkyl substituted by halogen;
R$^3$ is —(CH$_2$)$_p$-heterocyclyl optionally substituted by lower alkyl, halogen, —S(O)$_2$-lower alkyl, —C(O)-lower alkyl, —C(O)O-lower alkyl, hydroxy, lower alkyl substituted by hydroxy, —(CH$_2$)$_p$—O-lower alkyl, or —NHCO-lower alkyl, or is C$_{3-6}$-cycloalkyl optionally substituted by =O, —(CH$_2$)$_p$—O-lower alkyl or lower alkynyl, or is unsubstituted or substituted aryl or heteroaryl, wherein the substituents are selected from the group consisting of lower alkyl, CN, —S(O)$_2$-lower alkyl, halogen, —C(O)-lower alkyl, hydroxy, lower alkoxy and lower alkoxy substituted by halogen; or is —(CH$_2$)$_p$—NR$^4$R$^5$;

R$^4$ and R$^5$ are each independently hydrogen, lower alkyl, —(CRR')$_p$-lower alkyl substituted by hydroxy, —(CRR')$_p$—O-lower alkyl, —(CRR')$_p$—S-lower alkyl, —(CRR')$_p$—O-lower alkyl substituted by hydroxy, or C$_{3-6}$-cycloalkyl;

R and R' are each independently hydrogen, lower alkyl or lower alkyl substituted by hydroxyl;

n is 1 or 2;

o is 1 or 2; and p is 0, 1, 2, 3 or 4;

and pharmaceutically active acid-addition salts thereof.

The compounds of formula I can contain asymmetric carbon atoms. Accordingly, the present invention includes all stereoisomeric forms of the compounds of formula I, including each of the individual enantiomers and mixtures thereof.

Preferred are the trans-diastereoisomers, including both enantiomers as follows:

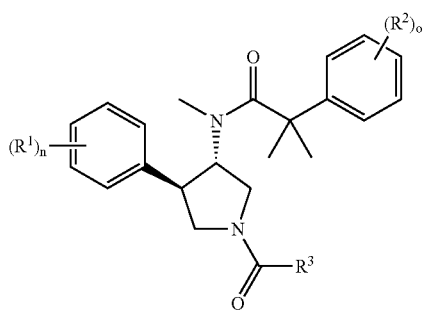

I

The present invention also provides compositions containing a compound of formula I and a pharmaceutically acceptable carrier. It further provides methods for the manufacture of compounds of formula I and the compositions containing them.

The compounds of formula I and their salts are characterized by valuable therapeutic properties. Compounds of formula I have a high affinity simultaneously to both the NK1 and the NK3 receptors (dual NK1/NK3 receptor antagonists), useful in the treatment of schizophrenia. Thus, the invention further provides a method for the treatment of schizophrenia which comprises administering to an individual a therapeutically effective amount of a compound of formula I.

DETAILED DESCRIPTION OF THE INVENTION

The following definitions of the general terms used in the present description apply irrespective of whether the terms in question appear alone or in combination.

As used herein, the term "lower alkyl" denotes a straight- or branched-chain alkyl group containing from 1-4 carbon atoms, for example methyl, ethyl, propyl, isopropyl, n-butyl, i-butyl, t-butyl and the like. The term "alkyl" denotes a straight- or branched-chain alkyl group containing from 1-7 carbon atoms, The term "halogen" denotes chlorine, iodine, fluorine and bromine.

The term "cycloalkyl" denotes a saturated carbocyclic group, containing 3-6 carbon atoms.

The term "heterocyclyl" denotes a saturated or partially saturated ring or ring-system, containing one or more heteroatoms, selected from N, O and S, with the rest of the ring atoms being carbon, for example morpholinyl, thiomorpholinyl, 1,1-dioxo-1-thiomorpholinyl, piperazin-1-yl, pyrrolidin-1-yl, pyrrolidin-2-yl piperidin-1-yl, piperidin-4-yl, azetidin-1-yl, tetrahydrofuran-2-yl, 2'-oxo-2',3'-dihydro-1H, 1'H-spiro[piperidine-4,4'-quinolin]-1-yl or 1-oxo-2,3-dihydro-1H,1'H-spiro[isoquinoline-4,4'-piperidin]-1'-yl.

The term "aryl" denotes a monovalent cyclic aromatic hydrocarbon radical consisting of one or more fused rings in which at least one ring is aromatic in nature, for example phenyl or naphthyl.

The term "heteroaryl" denotes a monovalent aromatic cyclic radical, containing one or more heteroatoms, selected from N, O and S, with the rest of the ring atoms being carbon, for example pyridyl, pyrazinyl, pyrimidinyl, pyridazinyl, triazinyl, thiazolyl, thienyl, furyl, pyrrolyl, imidazolyl, pyrazolyl, oxazolyl, isothiazolyl or isoxazolyl, preferred are the pyridyl and the pyrimidinyl groups.

"Pharmaceutically acceptable" such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

One embodiment for the present invention is compounds of formula I-A

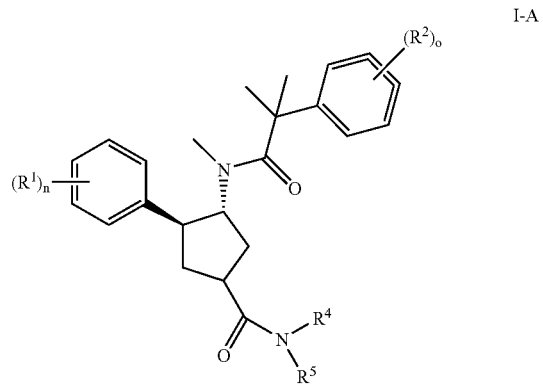

I-A wherein

R$^1$ is hydrogen, halogen or lower alkyl;

R$^2$ is hydrogen, halogen, lower alkoxy or lower alkyl substituted by halogen;

R$^4$ and R$^5$ are each independently hydrogen, lower alkyl, —(CRR')$_p$-lower alkyl substituted by hydroxy, —(CRR')$_p$—O-lower alkyl, —(CRR')$_p$—S-lower alkyl, —(CRR')$_p$—O-lower alkyl substituted by hydroxy, or C$_{3-6}$-cycloalkyl;

R and R' are each independently hydrogen, lower alkyl or lower alkyl substituted by hydroxy;

n is 1 or 2;
o is 1 or 2; and
p is 0, 1, 2, 3 or 4;

and pharmaceutically active acid-addition salts thereof.

Another embodiment for the present invention is compounds of formula I-B

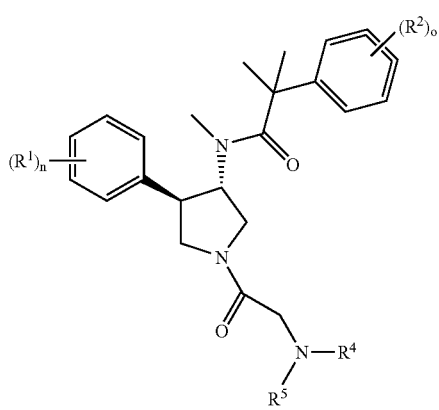

I-B wherein
R¹ is hydrogen, halogen or lower alkyl;
R² is hydrogen, halogen, lower alkoxy or lower alkyl substituted by halogen;
R⁴ and R⁵ are each independently hydrogen, lower alkyl, —(CRR')$_p$-lower alkyl substituted by hydroxy, —(CRR')$_p$—O-lower alkyl, —(CRR')$_p$—S-lower alkyl, —(CRR')$_p$—O-lower alkyl substituted by hydroxy, or $C_{3-6}$-cycloalkyl;
R and R' are each independently hydrogen, lower alkyl or lower alkyl substituted by hydroxy;
n is 1 or 2;
o is 1 or 2; and
p is 0, 1, 2, 3 or 4;

and pharmaceutically active acid-addition salts thereof.

Another embodiment for the present invention are compounds of formula I-C

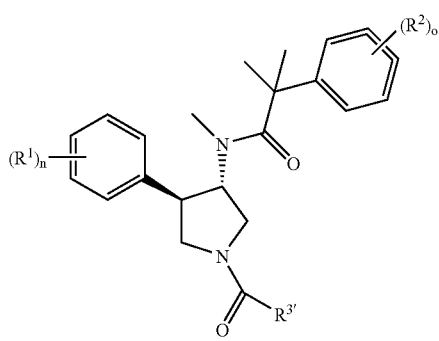

I-C wherein
R¹ is hydrogen, halogen or lower alkyl;
R² is hydrogen, halogen, lower alkoxy or lower alkyl substituted by halogen;
R³ is —(CH₂)$_p$-heterocyclyl optionally substituted by lower alkyl, halogen, —S(O)₂-lower alkyl, —C(O)-lower alkyl, —C(O)O-lower alkyl, hydroxy, lower alkyl substituted by hydroxy, —(CH₂)$_p$—O-lower alkyl or —NHCO-lower alkyl;
n is 1 or 2;
o is 1 or 2; and
p is 0, 1, 2, 3 or 4;

and pharmaceutically active acid-addition salts thereof.

A preferred group of compounds of formula I are those, wherein the substituent (R²)$_o$ is 3,5-di-CF₃.

Preferred compounds from this group are compounds, wherein R³ is morpholinyl, for example rac-2-(3,5-bis-trifluoromethyl-phenyl)-N-[(3S,4R)-4-(4-chloro-phenyl)-1-(morpholine-4-carbonyl)-pyrrolidin-3-yl]-N-methyl-isobutyramide, rac-2-(3,5-dichloro-phenyl)-N-[(3S,4R)-4-(4-fluoro-phenyl)-1-(morpholine-4-carbonyl)-pyrrolidin-3-yl]-N-methyl-isobutyramide and rac-2-(3,5-bis-trifluoromethyl-phenyl)-N-[(3S,4R)-4-(4-fluoro-2-methyl-phenyl)-1-(morpholine-4-carbonyl)-pyrrolidin-3-yl]-N-methyl-isobutyramide.

Further preferred are compounds, wherein R³ is piperazinyl, substituted by S(O)₂-lower alkyl or C(O)-lower alkyl, for example rac-2-(3,5-bis-trifluoromethyl-phenyl)-N-[(3S,4R)-4-(4-fluoro-phenyl)-1-(4-methanesulfonyl-piperazine-1-carbonyl)-pyrrolidin-3-yl]-N-methyl-isobutyramide, rac-N-[(3S,4R)-1-(4-acetyl-piperazine-1-carbonyl)-4-(4-fluoro-phenyl)-pyrrolidin-3-yl]-2-(3,5-bis-trifluoromethyl-phenyl)-N-methyl-isobutyramide, rac-2-(3,5-bis-trifluoromethyl-phenyl)-N-[(3S,4R)-1-(4-methanesulfonyl-piperazine-1-carbonyl)-4-phenyl-pyrrolidin-3-yl]-N-methyl-isobutyramide, rac-2-(3,5-dichloro-phenyl)-N-[(3S,4R)-4-(4-fluoro-phenyl)-1-(4-methanesulfonyl-piperazine-1-carbonyl)-pyrrolidin-3-yl]-N-methyl-isobutyramide, rac-2-(3,5-bis-trifluoromethyl-phenyl)-N-[(3S,4R)-4-(4-fluoro-2-methyl-phenyl)-1-(4-methanesulfonyl-piperazine-1-carbonyl)-pyrrolidin-3-yl]-N-methyl-isobutyramide and rac-N-[(3S,4R)-4-(4-chloro-phenyl)-1-(4-methanesulfonyl-piperazine-1-carbonyl)-pyrrolidin-3-yl]-2-(3,5-dichloro-phenyl)-N-methyl-isobutyramide.

Preferred compounds are further those, wherein R³ is NR⁴R⁵ for R⁴ and R⁵ being hydrogen or lower alkyl substituted by hydroxy, for example rac-(3S,4R)-3-{[2-(3,5-bis-trifluoromethyl-phenyl)-2-methyl-propionyl]-methyl-amino}-4-(4-fluoro-phenyl)-pyrrolidine-1-carboxylic acid bis-(2-hydroxy-ethyl)-amide and rac-(3S,4R)-3-{[2-(3,5-bis-trifluoromethyl-phenyl)-2-methyl-propionyl]-methyl-amino}-4-(4-fluoro-phenyl)-pyrrolidine-1-carboxylic acid (2-hydroxy-ethyl)-amide.

The present compounds of formula I and their pharmaceutically acceptable salts can be prepared by methods known in the art, described in general schemes 1 and 2 and in specific examples 1 to 62 and, for example, by a process described below, which process comprises a) reacting a compound of formula

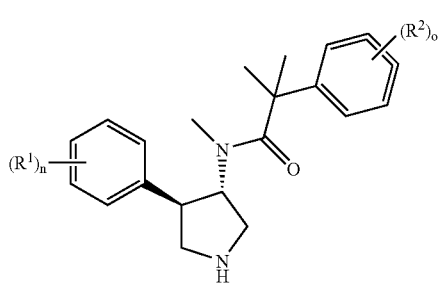

with a compound of formula

R³C(O)Cl to obtain a compound of formula

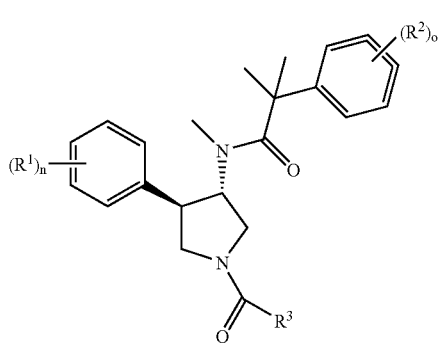

wherein the definitions are as described above, or b) reacting a compound of formula

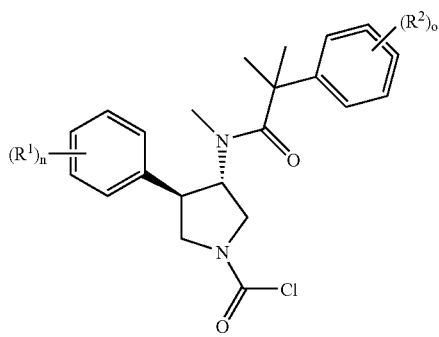

with an amine of formula

NHR⁴R⁵ to obtain a compound of formula

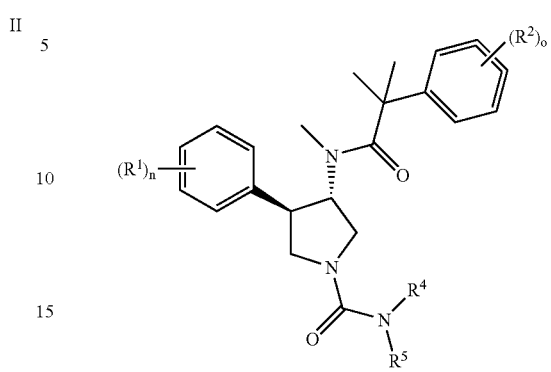

wherein $R^1$, $R^2$, $R^4$ and $R^5$ have the significances given above, or c) reacting a compound of formula

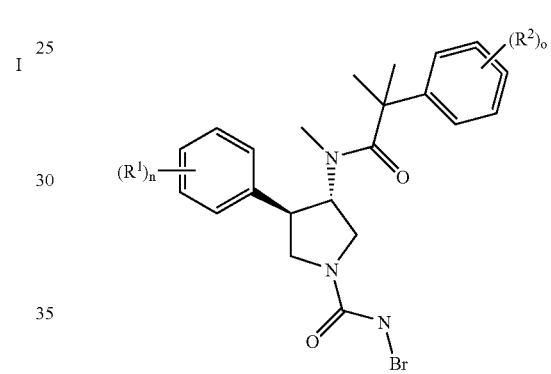

with an amine of formula

NHR⁴R⁵ to obtain a compound of formula

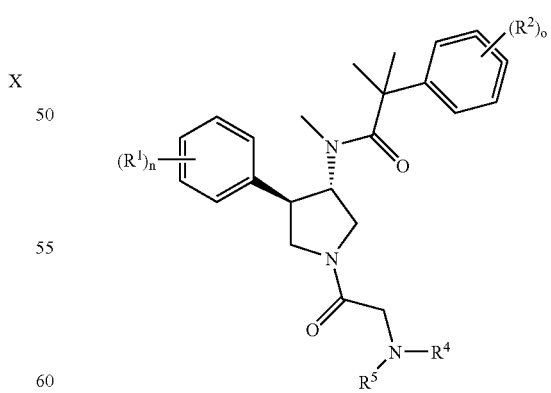

wherein $R^1$, $R^2$, $R^4$ and $R^5$ have the significances given above, and if desired, converting the compound obtained into a pharmaceutically acceptable acid addition salt.

In the schemes and in the description of the examples the following abbreviations have been used:

TFA=trifluoroacetic acid

THF=tetrahydrofuran

RT=room temperature

General scheme 1

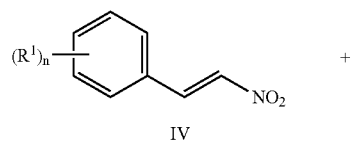
IV

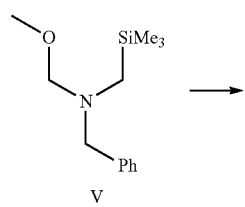
V

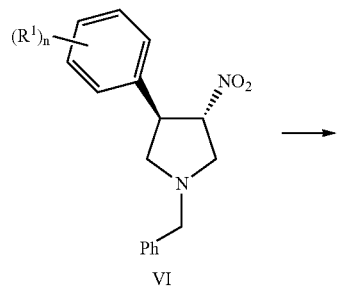
VI

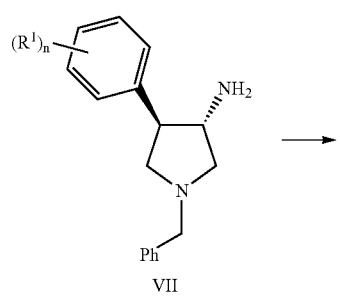
VII

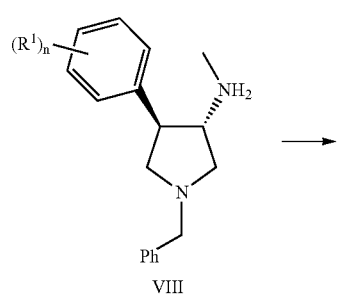
VIII

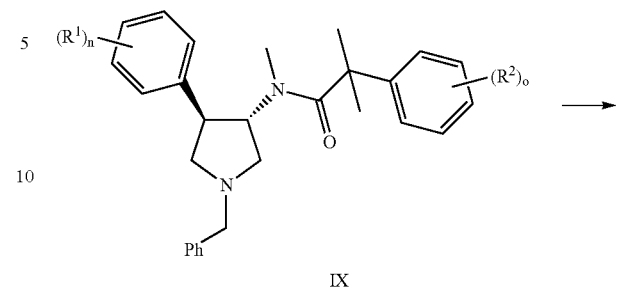
IX

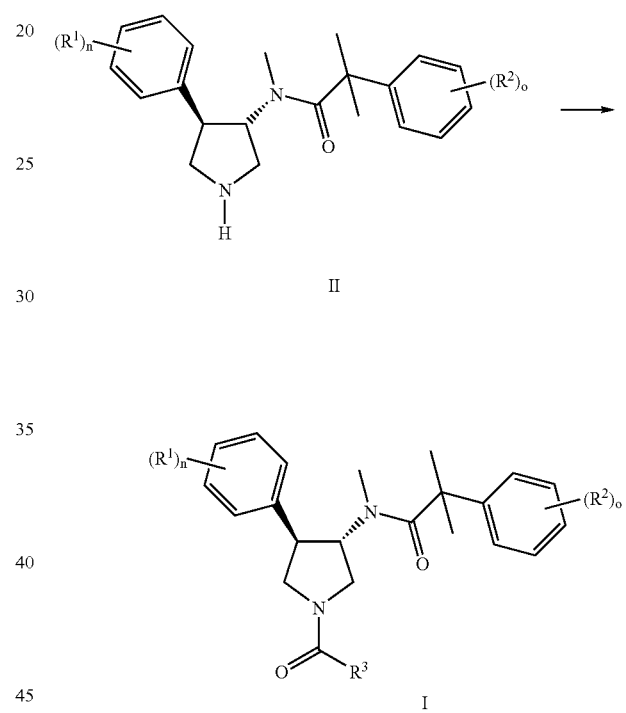
II

I

The pyrrolidines VI were prepared via a stereo specific 1,3-dipolar cycloaddition between the 2-nitrostyrene derivative IV and the azomethine ylide generated in situ from the N-(methoxymethyl)-N-(phenylmethyl)-N-(trimethylsilyl) methylamine V in the presence of a catalytic amount of acid, such as TFA. Reduction of the nitro moiety using standard conditions for example $SnCl_2.H_2O$ yielded VII. The amino moiety was subsequently methylated in a two step sequence, involving first the preparation of the ethyl carbamate followed by its reduction with borane to produce VIII. Reaction of VIII with an acid chloride in a presence of a base, usually $Et_3N$, yielded IX. Selective N-debenzylation was then carried out using several known procedures which are compatible with the substitution patterns of the aromatic rings to afford II. Finally derivatives I were prepared via a coupling with a suitable carbamoyl chloride, acid chloride or carboxylic acide.

General scheme 2

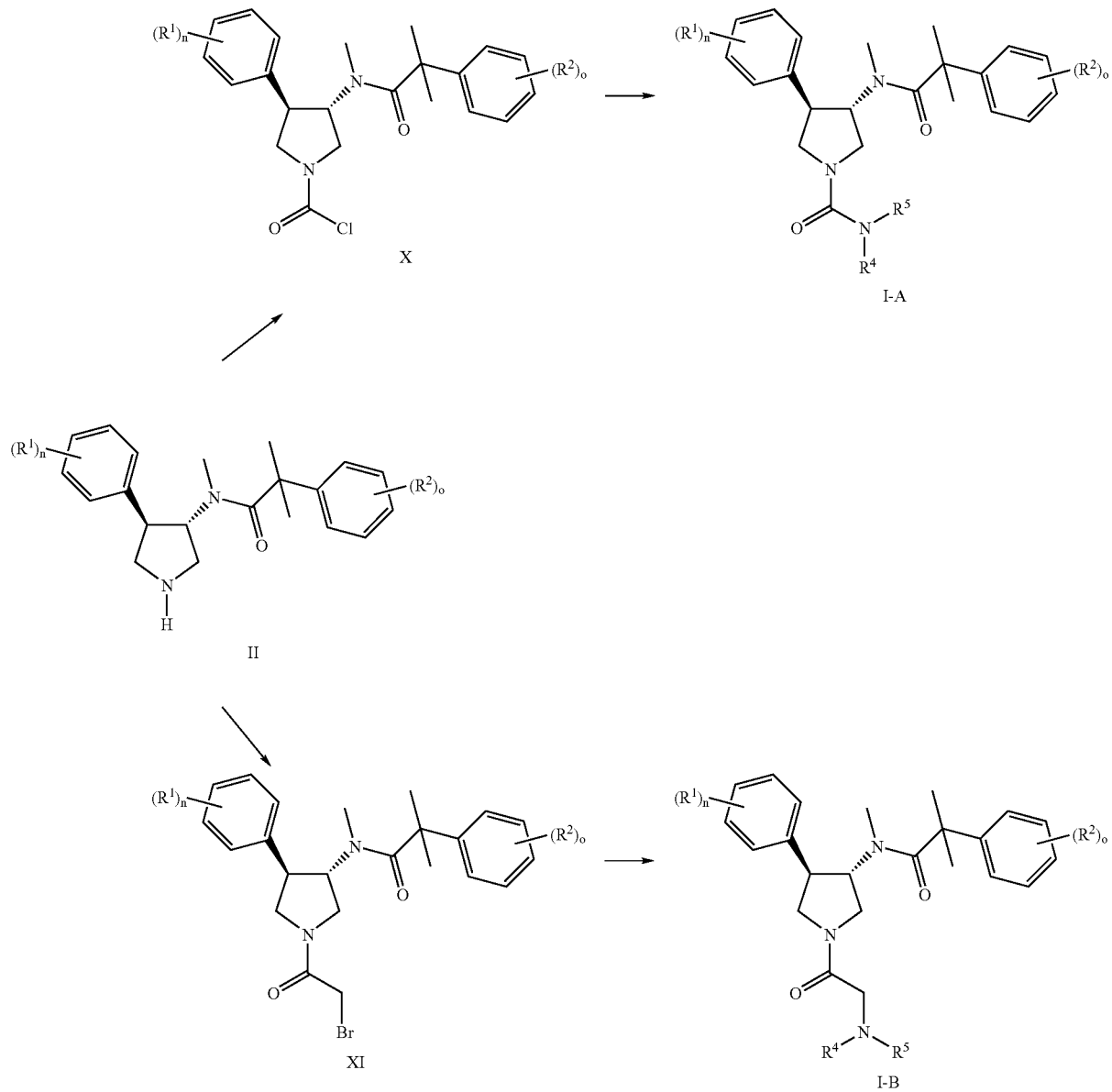

Alternatively, intermediates II could be converted in a two step sequence into final compound I-A or I-B. For instance, the treatment of derivatives II with triphosgene in a presence of a base, preferably pyridine and at low temperature yielded pyrrolidine-1-carbonyl chloride derivatives X. The coupling between compounds X and a primary or secondary amine gave access to urea of formula I-A. The treatment of derivatives II with bromo-acetyl chloride in a presence of a base yielded intermediates XI. A nucleophilic substitution reaction between XI and a primary or secondary amine gave access to amide of formula I-B.

As mentioned earlier, the compounds of formula I and their pharmaceutically usable addition salts possess valuable pharmacological properties. The compounds of the present invention are dual antagonists of the Neurokinin 1 and 3 receptors.

The compounds were investigated in accordance with the tests given hereinafter.

$NK_1$

The affinity of test compounds for the $NK_1$ receptor was evaluated at human $NK_1$ receptors in CHO cells infected with the human $NK_1$ receptor (using the Semliki virus expression system) and radiolabelled with [$^3$H]substance P (final concentration 0.6 nM). Binding assays were performed in HEPES buffer (50 mM, pH 7.4) containing BSA (0.04%) leupeptin (16.8 µg/ml), $MnCl_2$ (3 mM) and phosphoramidon (2 µM). Binding assays consisted of 250 µl of membrane suspension (approximately 1.5 µg/well in a 96 well plate), 0.125 µl of buffer of displacing agent and 125 µl of [$^3$H] substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 3×1 ml washes of HEPES buffer (50 mM, pH 7.4). The radioactivity retained on the filters was measured by scintillation counting. All assays were performed in duplicate in at least 2 separate experiments.

$NK_3$

Recombinant human $NK_3$ ($hNK_3$) receptor affinity was determined in a 96 well plate assay, using [$^3$H]SR142801 (final concentration 0.3 nM) to radiolabel the $hNK_3$ receptor in the presence of 10 concentrations of competing compound or buffer. Non specific binding was determined using 10 μM SB222200. Assay buffer consisted of Tris-HCl (50 mM, pH 7.4), BSA (0.1%), $MnCl_2$ (4 mM) and phosphoramidon (1 μM). Membrane preparations of hNK3 receptors (approximately 2.5 μg/well in a 96 well plate) were used to initiate the incubation for 90 min at room temperature. This assay was terminated by rapid filtration under vacuum through GF/C filters, presoaked for 90 min with PEI (0.3%), with 3×0.5 ml washes of ice-cold Tris buffer (50 mM, pH 7.4) containing 0.1% BSA. The radioactivity retained on the filters was measured by scintillation counting. All assays were performed in duplicate in at least two separate experiments.

The activity of the present compounds is described in the table below:

| Example No. | Ki NK1 (μM) | Ki NK3 (μM) |
| --- | --- | --- |
| 2 | 0.002348 | 0.4568 |
| 15 | 0.002057 | 0.155 |
| 16 | 0.001407 | 0.3091 |
| 21 | 0.001077 | 0.2038 |
| 22 | 0.000875 | 0.2034 |
| 23 | 0.001118 | 0.0924 |
| 24 | 0.001921 | 0.1998 |
| 26 | 0.000634 | 0.2116 |
| 27 | 0.000341 | 0.2756 |
| 28 | 0.000689 | 0.1373 |
| 55 | 0.003157 | 0.03 |

The present invention also provides pharmaceutical compositions containing compounds of the invention, for example compounds of formula I and their pharmaceutically suitable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following Examples illustrate the present invention without limiting it. All temperatures are given in degrees Celsius.

Example A

Tablets of the following composition can be manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition can be manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch can be firstly mixed in a mixer and then in a comminuting machine. The mixture then can be returned to the mixer, the talc can be added thereto and mixed thoroughly. The mixture can be filled by machine into hard gelatin capsules.

Example C

Suppositories of the following composition can be manufactured:

|  | mg/supp. |
| --- | --- |
| Active substance | 15 |
| Suppository mass | 1285 |
| Total | 1300 |

The suppository mass can be melted in a glass or steel vessel, mixed thoroughly and cooled to 45° C.

Thereupon, the finely powdered active substance can be added thereto and stirred until it has dispersed completely. The mixture then can be poured into suppository moulds of suitable size, left to cool, the suppositories are then removed from the moulds and packed individually in wax paper or metal foil.

Experimental Part

General procedure I

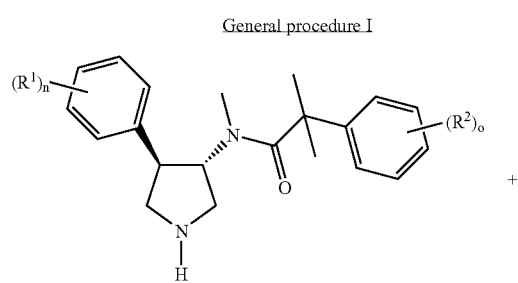

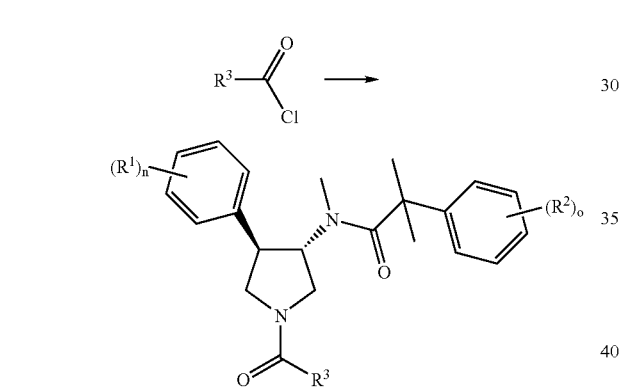

To a stirred solution of a pyrrolidine intermediate (1 mmol) in $CH_2Cl_2$ (15 ml) at RT were added ethyl-diisopropyl-amine (2 mmol) and a carbamoyl chloride or acid chloride of formula $R^3COCl$ (1.1 mmol). Stirring was continued until completion of the reaction. The reaction mixture was then concentrated under vacuo and purification by flash chromatography on $SiO_2$ or preparative HPLC.

General procedure II

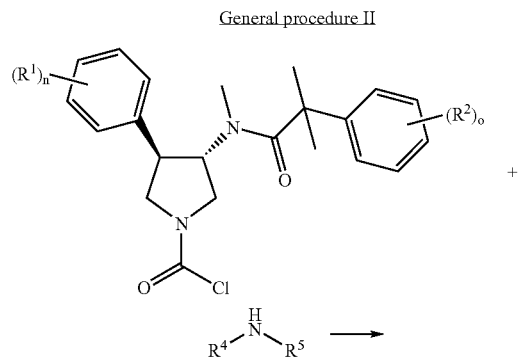

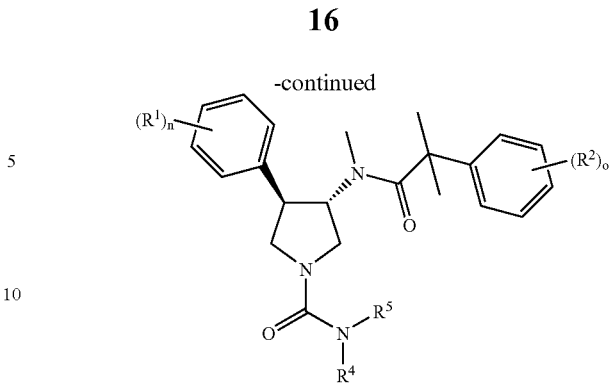

To a stirred solution of a pyrrolidine carbonyl chloride intermediate (1 mmol) in $CH_2Cl_2$ (15 ml) at RT were added ethyl-diisopropyl-amine (1.2 mmol) and a amine (1.1 mmol). Stirring was continued until completion of the reaction. The reaction mixture was then concentrated under vacuo and purification by flash chromatography on $SiO_2$ or preparative HPLC.

General procedure III

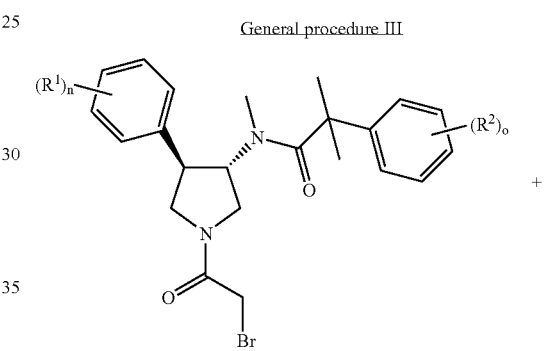

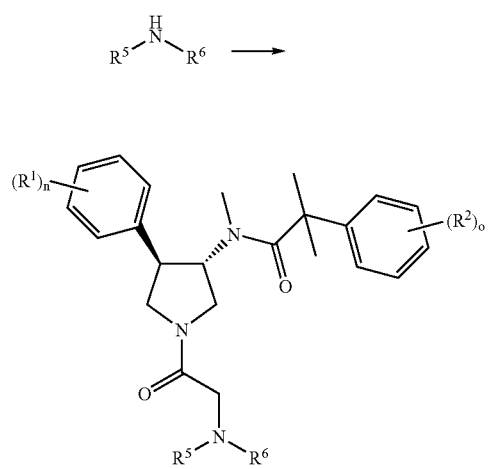

To a stirred solution of a pyrrolidine acetyl bromid intermediate (1 mmol) in THF (15 ml) at RT were added ethyl-diisopropyl-amine (1.2 mmol) and a amine (4 mmol). Stirring was continued until completion of the reaction. The reaction mixture was then concentrated under vacuo and purification by flash chromatography on $SiO_2$ or preparative HPLC.

Process for Preparation of Pyrrolidine Intermediates of Formula II

Pyrrolidine II-1 rac-2-(3,5-Bis-trifluoromethyl-phenyl)-N-methyl-N-((3S,4R)-4-phenyl-pyrrolidin-3-yl)-isobutyramide

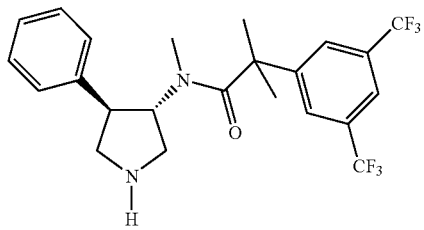

a) rac-(3S,4R)-1-Benzyl-3-nitro-4-phenyl-pyrrolidine (III-1)

A solution of N-(methoxymethyl)-N-(phenylmethyl)-N-(trimethylsilyl)methylamine (0.50 g, 2.02 mmol) in CH$_2$Cl$_2$ (15 ml) was added drop wise, over a 30 minutes period, to a stirred solution of ((E)-2-nitro-vinyl)-benzene (0.30 g, 2.02 mmol) and trifluoroacetic acid (0.17 ml, 0.2 mmol) in CH$_2$Cl$_2$ (10 ml) at 0° C. The ice bath was removed, and the solution was stirred at 25° C. for an additional 48 h. It was then concentrated and purification by flash chromatography (SiO$_2$, EtOAc/H 1:6) afforded 0.38 g (68%) of the title compound as a colorless oil. ES-MS m/e: 283 (M+H$^+$).

b) rac-(3S,4R)-1-Benzyl-4-phenyl-pyrrolidin-3-ylamine (IV-1)

To a stirred solution of rac-(3S,4R)-1-benzyl-3-nitro-4-phenyl-pyrrolidine (1.0 g, 3.54 mmol) in EtOAc (50 ml) was added in one portion SnCl$_2$.2H$_2$O (3.99 g, 17.70 mmol). The reaction mixture was then heated at reflux for 2 hours, cooled down to RT and a saturated aqueous solution of NaHCO$_3$ (100 ml) was added. The salts were filtered off and the product extracted with EtOAc. The organic phases were then dried over Na$_2$SO$_4$, and concentration under vacuum gave 0.72 g (80%) of rac-(3S,4R)-1-benzyl-4-phenyl-pyrrolidin-3-ylamine as a light yellow oil. The product was then used in the next step without further purification.

c) rac-((3S,4R)-1-Benzyl-4-phenyl-pyrrolidin-3-yl)-methyl-amine (V-1)

To a solution of rac-(3S,4R)-1-benzyl-4-phenyl-pyrrolidin-3-ylamine (0.25 g, 1.0 mmol) in THF (5 ml) was added a solution of K$_2$CO$_3$ (0.25 g, 1.8 mmol) in H$_2$O (2 ml). After 10 minutes, ethyl chloroformate (0.119 g, 1.1 mmol) was added and stirring was continued at RT for an additional 4 h. The intermediate carbamate was then extracted with Et$_2$O, dried over Na$_2$SO$_4$ and concentrated under vacuo to give viscous oil. The oil was taken up in THF (5 ml) and a solution of borane in THF (1M) was added (3.5 ml). The reaction mixture was then heated at 65° C. over night, cooled to RT and carefully quenched with conc. HCl (0.5 ml). The mixture was then heated at 80° C. for 2 h, cooled to RT, concentrated under vacuo, diluted with Et$_2$O (20 ml) and neutralized with an aqueous solution of NaHCO$_3$. The organic phases were dried over Na$_2$SO$_4$ and the product purified by flash chromatography (SiO$_2$, CH$_2$Cl$_2$/MeOH 9:1) to afford 0.21 g (82%) of rac-((3S,4R)-1-benzyl-4-phenyl-pyrrolidin-3-yl)-methyl-amine as a colorless oil.

d) rac-N-((3S,4R)-1-Benzyl-4-phenyl-pyrrolidin-3-yl)-2-(3,5-bis-trifluoromethyl-phenyl)-N-methyl-isobutyramide (VI-1)

A solution of 2-(3,5-bis-trifluoromethyl-phenyl)-2-methyl-propionyl chloride (the preparation of which is described in WO2002079134) (0.88 g, 2.76 mmol) in CH$_2$Cl$_2$ (2 ml) was added drop wise to a stirred solution of rac-((3S,4R)-1-benzyl-4-phenyl-pyrrolidin-3-yl)-methyl-amine (0.72 g, 2.70 mmol) and ethyl-diisopropyl-amine (0.64 ml, 3.76 mmol) in CH$_2$Cl$_2$ (5 ml). The reaction mixture was stirred 1 h, concentrated under vacuo and purification by flash chromatography (SiO$_2$, EtOAc/H, 1:4) yielded 1.05 g (74%) of the title product as colorless foam.

e) rac-2-(3,5-Bis-trifluoromethyl-phenyl)-N-methyl-N-((3S,4R)-4-phenyl-pyrrolidin-3-yl)-isobutyramide (VII-1)

To a solution of rac-N-((3S,4R)-1-Benzyl-4-phenyl-pyrrolidin-3-yl)-2-(3,5-bis-trifluoromethyl-phenyl)-N-methyl-isobutyramide (1.0 g, 1.82 mmol) in MeOH (30 ml) was added ammonium formate (0.59 g, 9.3 mmol) and Pd/C 10% (0.25 g). Stirring was continued at RT for 1 h, the reaction mixture was then filtered through celite, concentrated under vacuo. Purification by flash chromatography (SiO$_2$, CH$_2$Cl$_2$/MeOH 8:2) yielded 0.87 g (84%) of rac-2-(3,5-bis-trifluoromethyl-phenyl)-N-methyl-N-((3S,4R)-4-phenyl-pyrrolidin-3-yl)-isobutyramide as a colorless oil. ES-MS m/e: 459.4 (M+H$^+$).

Pyrrolidine II-2 rac-2-(3,5-Bis-trifluoromethyl-phenyl)-N-[(3S,4R)-4-(4-chloro-phenyl)-pyrrolidin-3-yl]-N-methyl-isobutyramide

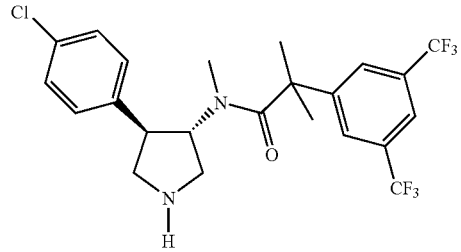

a) rac-(3R,4S)-1-Benzyl-3-(4-chloro-phenyl)-4-nitro-pyrrolidine (III-2)

A solution of N-(methoxymethyl)-N-(phenylmethyl)-N-(trimethylsilyl)methylamine (6.70 g, 28.2 mmol) in CH$_2$Cl$_2$ (100 ml) was added drop wise, over a 30 minutes period, to a stirred solution of 1-chloro-4-((E)-2-nitro-vinyl)-benzene (4.97 g, 27.1 mmol) and trifluoroacetic acid (0.31 g, 2.7 mmol) in CH$_2$Cl$_2$ (150 ml) at 0° C. The ice bath was removed, and the solution was stirred at 25° C. for an additional 48 h. It was then concentrated and purification by flash chromatography (SiO$_2$, EtOAc/H 1:4) afforded 6.75 g (79%) of the title compound as a colorless oil.

b) rac-(3S,4R)-1-Benzyl-4-(4-chloro-phenyl)-pyrrolidin-3-ylamine (IV-2)

Titanium (IV) chloride (0.36 g, 1.89 mmol) was added drop wise to a suspension of zinc powder (0.25 g, 3.78 mmol) in THF (3 ml). This solution was heated at 68° C. for one hour, then cooled to RT before rac-(3R,4S)-1-benzyl-3-(4-chloro-phenyl)-4-nitro-pyrrolidine (0.20 g, 0.63 mmol) in THF (2 ml) was added. The reaction mixture was then stirred at reflux over night. The reaction was cooled to RT, diluted with 300 ml of $Et_2O$, washed with an aqueous solution of $NaHCO_3$ and the organic phases were dried over $Na_2SO_4$. Flash chromatography ($SiO_2$, $CH_2Cl_2$/MeOH, 9:1) yielded 0.10 g (57%) of rac-(3S,4R)-1-benzyl-4-(4-chloro-phenyl)-pyrrolidin-3-ylamine as a light yellow oil.

c) rac-[(3S,4R)-1-Benzyl-4-(4-chloro-phenyl)-pyrrolidin-3-yl]-methyl-amine (V-2)

To a solution of rac-(3S,4R)-1-benzyl-4-(4-chloro-phenyl)-pyrrolidin-3-ylamine (1.86 g, 6.51 mmol) in THF (20 ml) was added a solution of $K_2CO_3$ (1.80 g, 13.02 mmol) in $H_2O$ (15 ml). After 10 minutes, ethyl chloroformate (0.68 ml, 7.16 mmol) was added and stirring was continued at RT for an additional 4 h. The intermediate carbamate was then extracted with $Et_2O$, dried over $Na_2SO_4$ and concentrated under vacuo to give viscous oil. The oil was taken up in THF (20 ml) and a solution of borane in THF (1M) was added (26 ml). The reaction mixture was then heated at 65° C. over night, cooled to RT and carefully quenched with conc. HCl (5 ml). The mixture was then heated at 80° C. for 2 h, cooled to RT, concentrated under vacuo, diluted with $Et_2O$ (100 ml) and neutralized with an aqueous solution of $NaHCO_3$. The organic phases were dried over $Na_2SO_4$ and the product purified by flash chromatography ($SiO_2$, $CH_2Cl_2$/MeOH 9:1) to afford 1.51 g (77%) of rac-[(3S,4R)-1-benzyl-4-(4-chloro-phenyl)-pyrrolidin-3-yl]-methyl-amine_as a colorless oil.

d) rac-N-[(3S,4R)-1-Benzyl-4-(4-chloro-phenyl)-pyrrolidin-3-yl]-2-(3,5-bis-trifluoromethyl-phenyl)-N-methyl-isobutyramide (VI-2)

A solution of 2-(3,5-bis-trifluoromethyl-phenyl)-2-methyl-propionyl chloride (the preparation of which is described in WO2002079134) (1.05 g, 3.30 mmol) in $CH_2Cl_2$ (10 ml) was added drop wise to a stirred solution of rac-[(3S,4R)-1-benzyl-4-(4-chloro-phenyl)-pyrrolidin-3-yl]-methyl-amine_ (0.90 g, 3.00 mmol) and ethyl-diisopropyl-amine (0.77 ml, 4.50 mmol) in $CH_2Cl_2$ (10 ml). The reaction mixture was stirred 1 h, concentrated under vacuo and purification by flash chromatography ($SiO_2$, EtOAc/H, 1:4) yielded 1.53 g (87%) of the title product as light brown oil.

e) rac-2-(3,5-Bis-trifluoromethyl-phenyl)-N-[(3S,4R)-4-(4-chloro-phenyl)-pyrrolidin-3-yl]-N-methyl-isobutyramide (VII-2)

To a solution of rac-N-[(3S,4R)-1-benzyl-4-(4-chloro-phenyl)-pyrrolidin-3-yl]-2-(3,5-bis-trifluoromethyl-phenyl)-N-methyl-isobutyramide_(1.46 g, 2.50 mmol) in toluene (15 ml) was added chloroethyl chloroformate (0.70 g, 5.00 mmol). Stirring was continued at 110° C. for 18 h, cooled to RT and MeOH (15 ml) was added. The solution was stirred at 80° C. over night, concentrated under vacuo, taken up in EtOAc, washed with an aqueous solution of $NaHCO_3$ and the organic phases dried over $Na_2SO_4$. Purification by flash chromatography ($SiO_2$, $CH_2Cl_2$/MeOH 95:5) yielded 0.52 g (42%) of rac-2-(3,5-bis-trifluoromethyl-phenyl)-N-[(3S,4R)-4-(4-chloro-phenyl)-pyrrolidin-3-yl]-N-methyl-isobutyramide_as a light brown oil. ES-MS m/e: 493.7 (M+H$^+$).

Pyrrolidine II-3 rac-N-[(3S,4R)-4-(4-Chloro-phenyl)-pyrrolidin-3-yl]-2-(3,5-dichloro-phenyl)-N-methyl-isobutyramide

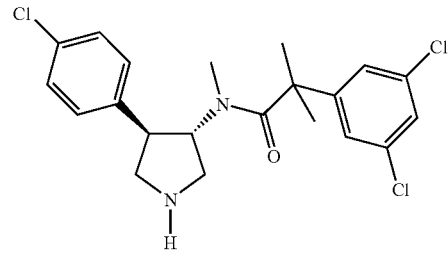

a) rac-N-[(3S,4R)-1-Benzyl-4-(4-chloro-phenyl)-pyrrolidin-3-yl]-2-(3,5-bis-trifluoromethyl-phenyl)-N-methyl-isobutyramide (VI-3)

A solution of 2-(3,5-Dichloro-phenyl)-2-methyl-propionyl chloride (the preparation of which is described in WO2005002577) (0.40 g, 1.59 mmol) in $CH_2Cl_2$ (5 ml) was added drop wise to a stirred solution of rac-[(3S,4R)-1-benzyl-4-(4-chloro-phenyl)-pyrrolidin-3-yl]-methyl-amine (the preparation of which is described herein above) (0.57 g, 1.90 mmol) and ethyl-diisopropyl-amine (0.41 ml, 2.38 mmol) in $CH_2Cl_2$ (10 ml). The reaction mixture was stirred 2 h, concentrated under vacuo and purification by flash chromatography ($SiO_2$, EtOAc/H, 1:4) yielded 0.25 g (31%) of the title product as light brown oil.

b) rac-N-[(3S,4R)-4-(4-Chloro-phenyl)-pyrrolidin-3-yl]-2-(3,5-dichloro-phenyl)-N-methyl-isobutyramide (VII-3)

To a solution of rac-N-[(3S,4R)-1-Benzyl-4-(4-chloro-phenyl)-pyrrolidin-3-yl]-2-(3,5-bis-trifluoromethyl-phenyl)-N-methyl-isobutyramide_(0.21 g, 0.41 mmol) in MeOH (20 ml) and $H_2O$ (10 ml) were added sodium hypophosphite monohydrate ($NaH_2PO_2.H_2O$, 87 mg, 0.82 mmol), a solution of sodium chloride (5 ml, 15 wt %) and Pd on charcoal (30 mg). Stirring was continued at 65° C. for 4 h, then at RT over night. The reaction mixture was filtered on celite, concentrated under vacuo and the product extracted with $CH_2Cl_2$. Purification by flash chromatography ($SiO_2$, $CH_2Cl_2$/MeOH 90:10) yielded 85 mg (48%) of rac-N-[(3S,4R)-4-(4-chloro-phenyl)-pyrrolidin-3-yl]-2-(3,5-dichloro-phenyl)-N-methyl-isobutyramide_as a light brown oil. ES-MS m/e: 427.2 (M+H$^+$).

Pyrrolidine II-4 rac-2-(3,5-Bis-trifluoromethyl-phenyl)-N-[(3S,4R)-4-(4-fluoro-phenyl)-pyrrolidin-3-yl]-N-methyl-isobutyramide

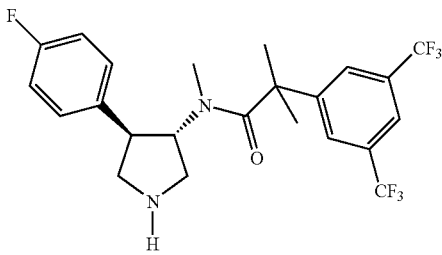

a) rac-(3R,4S)-1-Benzyl-3-(4-fluoro-phenyl)-4-nitro-pyrrolidine (III-4)

A solution of N-(methoxymethyl)-N-(phenylmethyl)-N-(trimethylsilyl)methylamine (8.00 g, 33.6 mmol) in $CH_2Cl_2$ (140 ml) was added drop wise, over a 30 minutes period, to a stirred solution of 1-fluoro-4-((E)-2-nitro-vinyl)-benzene (5.12 g, 30.6 mmol) and trifluoroacetic acid (0.23 ml, 3.1 mmol) in $CH_2Cl_2$ (200 ml) at 0° C. The ice bath was removed, and the solution was stirred at 25° C. for an additional 48 h. It was then concentrated and purification by flash chromatography ($SiO_2$, EtOAc/H 1:4) afforded 6.60 g (72%) of the title compound as a light yellow oil.

b) rac-(3S,4R)-1-Benzyl-4-(4-fluoro-phenyl)-pyrrolidin-3-ylamine (IV-4)

Titanium (IV) chloride (179.4 g, 0.94 mol) was added drop wise to a suspension of zinc powder (123.6 g, 1.89 mol) in THF (1200 ml). This solution was heated at 68° C. for one hour, then cooled to RT before rac-(3R,4S)-1-benzyl-3-(4-fluoro-phenyl)-4-nitro-pyrrolidine (94 g, 0.31 mol) in THF (400 ml) was added. The reaction mixture was then stirred at reflux over night. The reaction was cooled to RT, diluted with 3000 ml of $Et_2O$, washed with an aqueous solution of $NaHCO_3$ and the organic phases were dried over $Na_2SO_4$. Flash chromatography ($SiO_2$, $CH_2Cl_2$/MeOH, 9:1) yielded 18.9 g (22%) of rac-(3S,4R)-1-benzyl-4-(4-fluoro-phenyl)-pyrrolidin-3-ylamine as a brown oil.

c) rac-[(3S,4R)-1-Benzyl-4-(4-chloro-phenyl)-pyrrolidin-3-yl]-methyl-amine (V-4)

To a solution of rac-(3S,4R)-1-benzyl-4-(4-fluoro-phenyl)-pyrrolidin-3-ylamine (2.30 g, 8.50 mmol) in THF (25 ml) was added a solution of $K_2CO_3$ (2.35 g, 17.00 mmol) in $H_2O$ (17 ml). After 10 minutes, ethyl chloroformate (0.89 ml, 9.36 mmol) was added and stirring was continued at RT for an additional 2 h. The intermediate carbamate was then extracted with $Et_2O$, dried over $Na_2SO_4$ and concentrated under vacuo to give viscous oil. The oil was taken up in THF (25 ml) and a solution of borane in THF (1M) was added (34 ml). The reaction mixture was then heated at 65° C. over night, cooled to RT and carefully quenched with conc. HCl (5 ml). The mixture was then heated at 80° C. for 2 h, cooled to RT, concentrated under vacuo, diluted with $Et_2O$ (100 ml) and neutralized with an aqueous solution of $NaHCO_3$. The organic phases were dried over $Na_2SO_4$ and the product purified by flash chromatography ($SiO_2$, $CH_2Cl_2$/MeOH 9:1) to afford 0.69 g (29%) of rac-[(3S,4R)-1-benzyl-4-(4-fluoro-phenyl)-pyrrolidin-3-yl]-methyl-amine_as a colorless oil. ES-MS m/e: 285.1 (M+H+).

d) rac-N-[(3S,4R)-1-Benzyl-4-(4-fluoro-phenyl)-pyrrolidin-3-yl]-2-(3,5-bis-trifluoromethyl-phenyl)-N-methyl-isobutyramide (VI-4)

A solution of 2-(3,5-bis-trifluoromethyl-phenyl)-2-methyl-propionyl chloride (the preparation of which is described in WO2002079134) (0.88 g, 2.76 mmol) in $CH_2Cl_2$ (5 ml) was added drop wise to a stirred solution of rac-[(3S,4R)-1-benzyl-4-(4-fluoro-phenyl)-pyrrolidin-3-yl]-methyl-amine (0.72 g, 2.53 mmol) and ethyl-diisopropyl-amine (0.64 ml, 3.78 mmol) in $CH_2Cl_2$ (5 ml). The reaction mixture was stirred 1 h, concentrated under vacuo and purification by flash chromatography ($SiO_2$, EtOAc/H, 1:4) yielded 1.06 g (74%) of the title product as colorless foam. ES-MS m/e: 567.3 (M+H+).

e) rac-2-(3,5-Bis-trifluoromethyl-phenyl)-N-[(3S,4R)-4-(4-fluoro-phenyl)-pyrrolidin-3-yl]-N-methyl-isobutyramide (VII-4)

To a solution of rac-N-[(3S,4R)-1-benzyl-4-(4-fluoro-phenyl)-pyrrolidin-3-yl]-2-(3,5-bis-trifluoromethyl-phenyl)-N-methyl-isobutyramide (1.06 g, 1.87 mmol) in MeOH (30 ml) was added ammonium formate (0.59 g, 9.3 mmol) and Pd/C 10% (0.25 g). Stirring was continued at RT for 1 h, the reaction mixture was then filtered through celite, concentrated under vacuo. Purification by flash chromatography ($SiO_2$, $CH_2Cl_2$/MeOH 8:2) yielded 0.85 g (82%) of rac-2-(3,5-bis-trifluoromethyl-phenyl)-N-[(3S,4R)-4-(4-fluoro-phenyl)-pyrrolidin-3-yl]-N-methyl-isobutyramide_as a colorless oil. ES-MS m/e: 477.1 (M+H+).

Pyrrolidine II-5 rac-2-(3,5-Dichloro-phenyl)-N-[(3S,4R)-4-(4-fluoro-phenyl)-pyrrolidin-3-yl]-N-methyl-isobutyramide

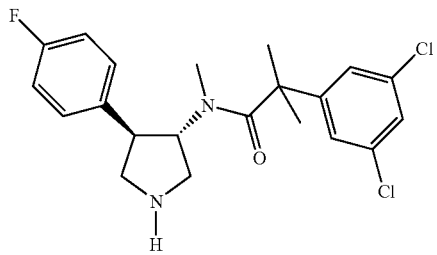

a) rac-N-[(3S,4R)-1-Benzyl-4-(4-fluoro-phenyl)-pyrrolidin-3-yl]-2-(3,5-dichloro-phenyl)-N-methyl-isobutyramide (VI-5)

A solution of 2-(3,5-dichloro-phenyl)-2-methyl-propionyl chloride (the preparation of which is described in WO2005002577) (0.146 g, 0.58 mmol) in $CH_2Cl_2$ (4 ml) was added drop wise to a stirred solution of rac-[(3S,4R)-1-benzyl-4-(4-fluoro-phenyl)-pyrrolidin-3-yl]-methyl-amine (the preparation of which is described herein above) (0.15 g, 0.52 mmol) and ethyl-diisopropyl-amine (0.13 ml, 0.79 mmol) in CH₂Cl₂ (5 ml). The reaction mixture was stirred 2 h, concentrated under vacuo and purification by flash chromatography (SiO₂, EtOAc/H, 1:4) yielded 0.18 g (68%) of the title product as light brown oil.

b) rac-N-[(3S,4R)-4-(4-Fluoro-phenyl)-pyrrolidin-3-yl]-2-(3,5-dichloro-phenyl)-N-methyl-isobutyramide (VII-5)

To a solution of rac-N-[(3S,4R)-1-benzyl-4-(4-fluoro-phenyl)-pyrrolidin-3-yl]-2-(3,5-dichloro-phenyl)-N-methyl-isobutyramide_(0.18 g, 0.36 mmol) in toluene (2 ml) was added chloroethyl chloroformate (77 mg, 0.54 mmol). Stirring was continued at 110° C. for 18 h, cooled to RT and MeOH (4 ml) was added. The solution was stirred at 80° C. over night, concentrated under vacuo, taken up in EtOAc, washed with an aqueous solution of NaHCO₃ and the organic phases dried over Na₂SO₄. Purification by flash chromatography (SiO₂, CH₂Cl₂/MeOH 90:10) yielded 90 mg (61%) of 2-(3,5-dichloro-phenyl)-N-[(3S,4R)-4-(4-fluoro-phenyl)-pyrrolidin-3-yl]-N-methyl-isobutyramide as a light brown oil. ES-MS m/e: 409.2 (M+H⁺).

Pyrrolidine II-6 rac-2-(3-Chloro-phenyl)-N-[(3S,4R)-4-(4-fluoro-phenyl)-pyrrolidin-3-yl]-N-methyl-isobutyramide

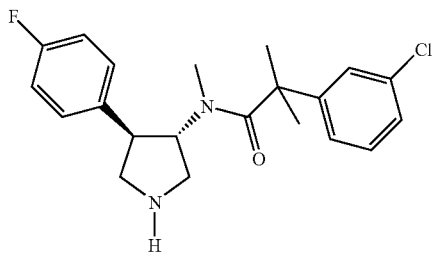

a) N-[(3S,4R)-1-Benzyl-4-(4-fluoro-phenyl)-pyrrolidin-3-yl]-2-(3-chloro-phenyl)-N-methyl-isobutyramide (VI-6)

A solution of 2-(3-chloro-phenyl)-2-methyl-propionyl chloride (the preparation of which is described in DE2659404) (0.10 g, 0.46 mmol) in CH₂Cl₂ (4 ml) was added drop wise to a stirred solution of rac-[(3S,4R)-1-benzyl-4-(4-fluoro-phenyl)-pyrrolidin-3-yl]-methyl-amine (the preparation of which is described herein above) (0.11 g, 0.38 mmol) and ethyl-diisopropyl-amine (0.10 ml, 0.58 mmol) in CH₂Cl₂ (5 ml). The reaction mixture was stirred 2 h, concentrated under vacuo and purification by flash chromatography (SiO₂, EtOAc/H, 1:3) yielded 0.14 g (80%) of the title product as light yellow oil. ES-MS m/e: 465.2 (M+H⁺).

b) rac-2-(3-Chloro-phenyl)-N-[(3S,4R)-4-(4-fluoro-phenyl)-pyrrolidin-3-yl]-N-methyl-isobutyramide (VII-6)

To a solution of N-[(3S,4R)-1-benzyl-4-(4-fluoro-phenyl)-pyrrolidin-3-yl]-2-(3-chloro-phenyl)-N-methyl-isobutyramide_(0.14 g, 0.31 mmol) in toluene (2 ml) was added chloroethyl chloroformate (66 mg, 0.46 mmol). Stirring was continued at 110° C. for 18 h, cooled to RT and MeOH (4 ml) was added. The solution was stirred at 80° C. over night, concentrated under vacuo, taken up in EtOAc, washed with an aqueous solution of NaHCO₃ and the organic phases dried over Na₂SO₄. Purification by flash chromatography (SiO₂, CH₂Cl₂/MeOH 90:10) yielded 33 mg (28%) of the title compound as light brown oil. ES-MS m/e: 375.3 (M+H⁺).

Pyrrolidine II-7 rac-2-(3,5-Bis-trifluoromethyl-phenyl)-N-[(3S,4R)-4-(4-fluoro-2-methyl-phenyl)-pyrrolidin-3-yl]-N-methyl-isobutyramide

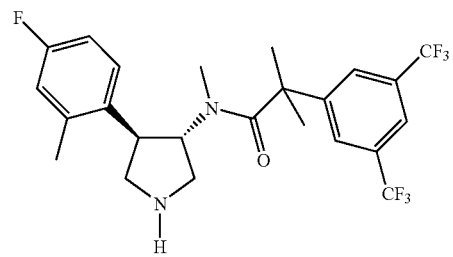

a) rac-(3R,4S)-1-Benzyl-3-(4-fluoro-2-methyl-phenyl)-4-nitro-pyrrolidine (III-7)

A solution of N-(methoxymethyl)-N-(phenylmethyl)-N-(trimethylsilyl)methylamine (1.95 g, 8.21 mmol) in CH₂Cl₂ (30 ml) was added drop wise, over a 30 minutes period, to a stirred solution of 4-fluoro-2-methyl-1-((E)-2-nitro-vinyl)-benzene (1.49 g, 8.22 mmol) and trifluoroacetic acid (0.60 ml, 0.82 mmol) in CH₂Cl₂ (30 ml) at 0° C. The ice bath was removed, and the solution was stirred at 25° C. for an additional 48 h. It was then concentrated and purification by flash chromatography (SiO₂, EtOAc/H 1:6) afforded 0.77 g (30%) of the title compound as a light yellow oil. ES-MS m/e: 315.2 (M+H⁺).

b) rac-(3S,4R)-1-Benzyl-4-(4-fluoro-2-methyl-phenyl)-pyrrolidin-3-ylamine (IV-7)

To a stirred solution of rac-(3R,4S)-1-benzyl-3-(4-fluoro-2-methyl-phenyl)-4-nitro-pyrrolidine (56 mg, 0.18 mmol) in EtOAc (5 ml) was added in one portion SnCl₂.2H₂O (201 mg, 0.89 mmol). The reaction mixture was then heated at reflux for 2 hours, cooled down to RT and a saturated aqueous solution of NaHCO₃ (100 ml) was added. The salts were filtered off and the product extracted with EtOAc. The organic phases were then dried over Na₂SO₄, and concentration under vacuum gave 40 mg (79%) of rac-(3S,4R)-1-benzyl-4-(4-fluoro-2-methyl-phenyl)-pyrrolidin-3-ylamine as a light yellow oil. The product was then used in the next step without further purification. ES-MS m/e: 285.3 (M+H⁺).

c) rac-[(3S,4R)-1-Benzyl-4-(4-fluoro-2-methyl-phenyl)-pyrrolidin-3-yl]-methyl-amine (V-7)

To a solution of rac-(3S,4R)-1-benzyl-4-(4-fluoro-2-methyl-phenyl)-pyrrolidin-3-ylamine (130 mg, 0.46 mmol) in THF (6 ml) was added a solution of K₂CO₃ (126 mg, 0.91 mmol) in H₂O (2 ml). After 10 minutes, ethyl chloroformate (0.05 ml, 0.48 mmol) was added and stirring was continued at RT for an additional 2 h. The intermediate carbamate was then extracted with Et$_2$O, dried over Na$_2$SO$_4$ and concentrated under vacuo to give viscous oil. The oil was taken up in THF (5 ml) and a solution of borane in THF (1M) was added (1.9 ml). The reaction mixture was then heated at 65° C. over night, cooled to RT and carefully quenched with conc. HCl (2 ml). The mixture was then heated at 80° C. for 2 h, cooled to RT, concentrated under vacuo, diluted with Et$_2$O (30 ml) and neutralized with an aqueous solution of NaHCO$_3$. The organic phases were dried over Na$_2$SO$_4$ and the product purified by flash chromatography (SiO$_2$, CH$_2$Cl$_2$/MeOH 9:1) to afford 77 mg (56%) of rac-[(3S,4R)-1-benzyl-4-(4-fluoro-2-methyl-phenyl)-pyrrolidin-3-yl]-methyl-amine as a colorless oil. ES-MS m/e: 299.3 (M+H$^+$).

d) rac-N-[(3S,4R)-1-Benzyl-4-(4-fluoro-2-methyl-phenyl)-pyrrolidin-3-yl]-2-(3,5-bis-trifluoromethyl-phenyl)-N-methyl-isobutyramide (VI-7)

A solution of 2-(3,5-bis-trifluoromethyl-phenyl)-2-methyl-propionyl chloride (the preparation of which is described in WO2002079134) (90 mg, 0.28 mmol) in CH$_2$Cl$_2$ (5 ml) was added drop wise to a stirred solution of rac-[(3S,4R)-1-benzyl-4-(4-fluoro-2-methyl-phenyl)-pyrrolidin-3-yl]-methyl-amine (77 mg, 0.26 mmol) and ethyl-diisopropyl-amine (0.07 ml, 0.38 mmol) in CH$_2$Cl$_2$ (5 ml). The reaction mixture was stirred 1 h, concentrated under vacuo and purification by flash chromatography (SiO$_2$, EtOAc/H, 1:4) yielded 80 mg (54%) of the title product as colorless oil. ES-MS m/e: 581.2 (M+H$^+$).

e) rac-2-(3,5-Bis-trifluoromethyl-phenyl)-N-[(3S,4R)-4-(4-fluoro-2-methyl-phenyl)-pyrrolidin-3-yl]-N-methyl-isobutyramide (VII-7)

To a solution of rac-N-[(3S,4R)-1-benzyl-4-(4-fluoro-2-methyl-phenyl)-pyrrolidin-3-yl]-2-(3,5-bis-trifluoromethyl-phenyl)-N-methyl-isobutyramide_(0.10 g, 0.17 mmol) in MeOH (5 ml) was added ammonium formate (43 mg, 0.68 mmol) and Pd/C 10% (20 mg). Stirring was continued at RT for 2.5 h, the reaction mixture was then filtered through celite, concentrated under vacuo. Purification by flash chromatography (SiO$_2$, CH$_2$Cl$_2$/MeOH 8:2) yielded 68 mg (80%) of the title compound as colorless oil. ES-MS m/e: 491.1 (M+H$^+$).

Pyrrolidine II-8 rac-2-(3,5-Bis-trifluoromethyl-phenyl)-N-methyl-N-((3S,4R)-4-o-tolyl-pyrrolidin-3-yl)-isobutyramide

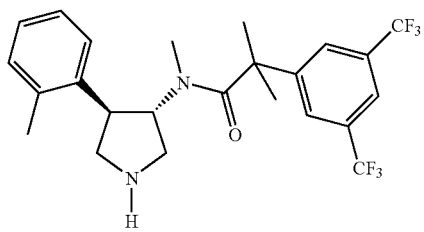

a) rac-(3S,4R)-1-Benzyl-3-nitro-4-o-tolyl-pyrrolidine (III-8)

A solution of N-(methoxymethyl)-N-(phenylmethyl)-N-(trimethylsilyl)methylamine (3.93 g, 16.55 mmol) in CH$_2$Cl$_2$ (60 ml) was added drop wise, over a 30 minutes period, to a stirred solution of 1-methyl-2-((E)-2-nitro-vinyl)-benzene (2.70 g, 16.55 mmol) and trifluoroacetic acid (0.13 ml, 1.65 mmol) in CH$_2$Cl$_2$ (30 ml) at 0° C. The ice bath was removed, and the solution was stirred at 25° C. for an additional 48 h. It was then concentrated and purification by flash chromatography (SiO$_2$, EtOAc/H 1:6) afforded 1.01 g (21%) of the title compound as a light yellow oil. ES-MS m/e: 297.4 (M+H$^+$).

b) rac-(3S,4R)-1-Benzyl-4-o-tolyl-pyrrolidin-3-ylamine (IV-8)

To a stirred solution of rac-(3S,4R)-1-benzyl-3-nitro-4-o-tolyl-pyrrolidine_(1.01 g, 3.40 mmol) in EtOAc (50 ml) was added in one portion SnCl$_2$.2H$_2$O (3.85 g, 17.04 mmol). The reaction mixture was then heated at reflux for 2 hours, cooled down to RT and a saturated aqueous solution of NaHCO$_3$ (100 ml) was added. The salts were filtered off and the product extracted with EtOAc. The organic phases were then dried over Na$_2$SO$_4$, and concentration under vacuum gave 0.73 g (81%) of rac-(3S,4R)-1-benzyl-4-o-tolyl-pyrrolidin-3-ylamine as a light yellow oil. The product was then used in the next step without further purification. ES-MS m/e: 267.4 (M+H$^+$).

c) rac-((3S,4R)-1-Benzyl-4-o-tolyl-pyrrolidin-3-yl)-methyl-amine (V-8)

To a solution of rac-(3S,4R)-1-benzyl-4-o-tolyl-pyrrolidin-3-ylamine (0.73 g, 2.74 mmol) in THF (15 ml) was added a solution of K$_2$CO$_3$ (0.75 mg, 5.48 mmol) in H$_2$O (5 ml). After 10 minutes, ethyl chloroformate (0.27 ml, 2.87 mmol) was added and stirring was continued at RT for an additional 2 h. The intermediate carbamate was then extracted with Et$_2$O, dried over Na$_2$SO$_4$ and concentrated under vacuo to give viscous oil. The oil was taken up in THF (10 ml) and a solution of borane in THF (1M) was added (11 ml). The reaction mixture was then heated at 65° C. over night, cooled to RT and carefully quenched with conc. HCl (5 ml). The mixture was then heated at 80° C. for 2 h, cooled to RT, concentrated under vacuo, diluted with Et$_2$O (60 ml) and neutralized with an aqueous solution of NaHCO$_3$. The organic phases were dried over Na$_2$SO$_4$ and the product purified by flash chromatography (SiO$_2$, CH$_2$Cl$_2$/MeOH 9:1) to afford 0.27 g (35%) of rac-((3S,4R)-1-benzyl-4-o-tolyl-pyrrolidin-3-yl)-methyl-amine as a colorless oil. ES-MS m/e: 281.3 (M+H$^+$).

d) rac-N-((3S,4R)-1-Benzyl-4-o-tolyl-pyrrolidin-3-yl)-2-(3,5-bis-trifluoromethyl-phenyl)-N-methyl-isobutyramide (VI-8)

A solution of 2-(3,5-bis-trifluoromethyl-phenyl)-2-methyl-propionyl chloride (the preparation of which is described in WO2002079134) (170 mg, 0.53 mmol) in CH$_2$Cl$_2$ (5 ml) was added drop wise to a stirred solution of rac-((3S,4R)-1-benzyl-4-o-tolyl-pyrrolidin-3-yl)-methyl-amine_(135 mg, 0.48 mmol) and ethyl-diisopropyl-amine (0.12 ml, 0.72 mmol) in CH$_2$Cl$_2$ (5 ml). The reaction mixture was stirred 1 h, concentrated under vacuo and purification by flash chromatography (SiO$_2$, EtOAc/H, 1:3) yielded 180 mg (66%) of the title product as colorless oil. ES-MS m/e: 563.7 (M+H$^+$).

e) rac-2-(3,5-Bis-trifluoromethyl-phenyl)-N-[(3S, 4R)-4-(4-fluoro-2-methyl-phenyl)-pyrrolidin-3-yl]-N-methyl-isobutyramide (VII-8)

To a solution of rac-N-((3S,4R)-1-benzyl-4-o-tolyl-pyrrolidin-3-yl)-2-(3,5-bis-trifluoromethyl-phenyl)-N-methyl-isobutyramide_(0.10 g, 0.17 mmol) in MeOH (5 ml) was added ammonium formate (45 mg, 0.71 mmol) and Pd/C 10% (20 mg). Stirring was continued at RT for 2.5 h, the reaction mixture was then filtered through celite, concentrated under vacuo. Purification by flash chromatography (SiO$_2$, CH$_2$Cl$_2$/MeOH 8:2) yielded 75 mg (89%) of the title compound as colorless oil. ES-MS m/e: 473.3 (M+H$^+$).

Pyrrolidine II-9 rac-2-(3,5-Dichloro-phenyl)-N-methyl-N-((3S,4R)-4-o-tolyl-pyrrolidin-3-yl)-isobutyramide

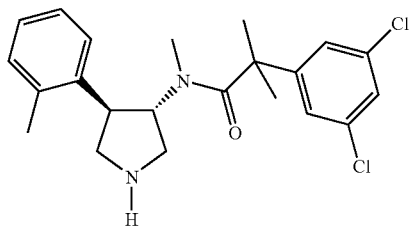

a) rac-N-((3S,4R)-1-Benzyl-4-o-tolyl-pyrrolidin-3-yl)-2-(3,5-dichloro-phenyl)-N-methyl-isobutyramide (VI-9)

A solution of 2-(3,5-dichloro-phenyl)-2-methyl-propionyl chloride (the preparation of which is described in WO2005002577) (127 mg, 0.50 mmol) in CH$_2$Cl$_2$ (5 ml) was added drop wise to a stirred solution of ((3S,4R)-1-benzyl-4-o-tolyl-pyrrolidin-3-yl)-methyl-amine (the preparation of which is described herein above) (135 mg, 0.48 mmol) and ethyl-diisopropyl-amine (0.12 ml, 0.72 mmol) in CH$_2$Cl$_2$ (5 ml). The reaction mixture was stirred 2 h, concentrated under vacuo and purification by flash chromatography (SiO$_2$, EtOAc/H, 1:3) yielded 0.18 g (75%) of the title product as colorless oil.

b) rac-2-(3,5-Dichloro-phenyl)-N-methyl-N-((3S, 4R)-4-o-tolyl-pyrrolidin-3-yl)-isobutyramide (VII-9)

To a solution of _rac-N-((3S,4R)-1-benzyl-4-o-tolyl-pyrrolidin-3-yl)-2-(3,5-dichloro-phenyl)-N-methyl-isobutyramide_(0.18 g, 0.36 mmol) in toluene (2 ml) was added chloroethyl chloroformate (78 mg, 0.54 mmol). Stirring was continued at 110° C. for 18 h, cooled to RT and MeOH (4 ml) was added. The solution was stirred at 80° C. over night, concentrated under vacuo, taken up in EtOAc, washed with an aqueous solution of NaHCO$_3$ and the organic phases were dried over Na$_2$SO$_4$. Purification by flash chromatography (SiO$_2$, CH$_2$Cl$_2$/MeOH 90:10) yielded 35 mg (24%) of rac-2-(3,5-dichloro-phenyl)-N-methyl-N-((3S,4R)-4-o-tolyl-pyrrolidin-3-yl)-isobutyramide as_a light yellow oil. ES-MS m/e: 405.3 (M+H$^+$).

Pyrrolidine Intermediates of Formula X

Pyrrolidine X-1 rac-(3S,4R)-3-{[2-(3,5-Bis-trifluoromethyl-phenyl)-2-methyl-propionyl]-methyl-amino}-4-phenyl-pyrrolidine-1-carbonyl chloride

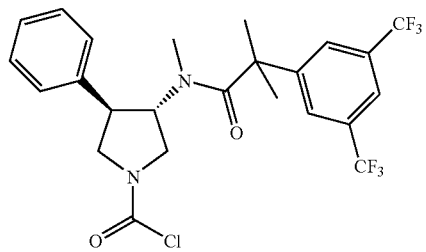

To a stirred solution of carbonic acid ditrichloromethyl ester (triphosgene) (106 mg, 0.36 mmol) in CH$_2$Cl$_2$ (15 ml) at −78° C., was added a solution of rac-2-(3,5-bis-trifluoromethyl-phenyl)-N-methyl-N-((3S,4R)-4-phenyl-pyrrolidin-3-yl)-isobutyramide (Intermediate VII-1), (410 mg, 0.89 mmol) and pyridine (0.16 ml, 1.97 mmol) in CH$_2$Cl$_2$ (5 ml) over 30 minutes. The temperature was raised to RT, and stirring was continued for 2 hours. The organic phase was washed with H$_2$O, dried over Na$_2$SO$_4$. Purification by flash chromatography (SiO$_2$, EtOAc/Hx 1:1) yielded 428 mg (92%) of the title compound as_colorless oil.

ES-MS m/e: 521.2 (M+H$^+$).

Pyrrolidine X-4 rac-((3S,4R)-3-{[2-(3,5-Bis-trifluoromethyl-phenyl)-2-methyl-propionyl]-methyl-amino}-4-(4-fluoro-phenyl)-pyrrolidine-1-carbonyl chloride

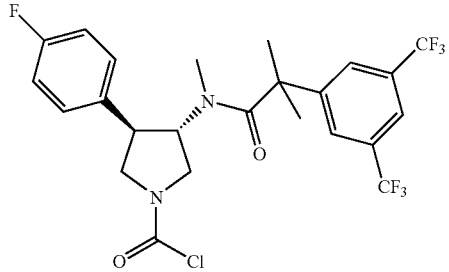

To a stirred solution of carbonic acid ditrichloromethyl ester (triphosgene) (31 mg, 0.10 mmol) in CH$_2$Cl$_2$ (5 ml) at 0° C., was added a solution of rac-2-(3,5-bis-trifluoromethyl-phenyl)-N-[(3S,4R)-4-(4-fluoro-phenyl)-pyrrolidin-3-yl]-N-methyl-isobutyramide (Intermediate VII-4), (100 mg, 0.21 mmol) and pyridine (0.02 ml, 0.22 mmol) in CH$_2$Cl$_2$ (2 ml) over 30 minutes. The temperature was raised to RT, and stirring was continued for 2 hours. The organic phase was washed with H$_2$O, dried over Na$_2$SO$_4$. Purification by flash chromatography (SiO$_2$, EtOAc/Hx 1:1) yielded 25 mg (22%) of the title compound as colorless oil.
ES-MS m/e: 539.3 (M+H$^+$).

Pyrrolidine X-5 rac-(3S,4R)-3-{[2-(3,5-Dichloro-phenyl)-2-methyl-propionyl]-methyl-amino}-4-(4-fluoro-phenyl)-pyrrolidine-1-carbonyl chloride

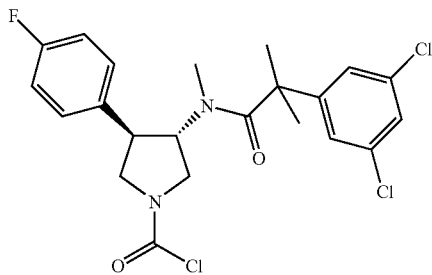

To a stirred solution of carbonic acid ditrichloromethyl ester (triphosgene) (12 mg, 0.040 mmol) in CH$_2$Cl$_2$ (3 ml) at −78° C., was added a solution of rac-2-(3,5-dichloro-phenyl)-N-[(3S,4R)-4-(4-fluoro-phenyl)-pyrrolidin-3-yl]-N-methyl-isobutyramide (Intermediate VII-5), (41 mg, 0.10 mmol) and pyridine (0.02 ml, 0.22 mmol) in CH$_2$Cl$_2$ (2 ml) over 30 minutes. The temperature was raised to RT, and stirring was continued for 2 hours. The organic phase was washed with H$_2$O, dried over Na$_2$SO$_4$. Purification by flash chromatography (SiO$_2$, EtOAc/Hx 1:1) yielded 37 mg (79%) of the title compound as colorless oil.
ES-MS m/e: 473.0 (M+H$^+$).

Pyrrolidine Intermediates of Formula XI

Pyrrolidine XI-4 rac-2-(3,5-Bis-trifluoromethyl-phenyl)-N-[(3S,4R)-1-(2-bromo-acetyl)-4-(4-fluoro-phenyl)-pyrrolidin-3-yl]-N-methyl-isobutyramide

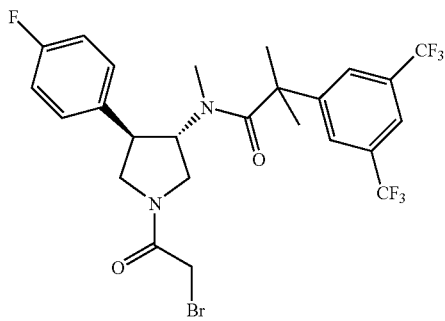

To a stirred solution of bromo-acetyl chloride (0.80 g, 4 mmol) in CH$_2$Cl$_2$ (5 ml) at 0° C. was added over 1 hour a solution of rac-2-(3,5-bis-trifluoromethyl-phenyl)-N-[(3S,4R)-4-(4-fluoro-phenyl)-pyrrolidin-3-yl]-N-methyl-isobutyramide (pyrrolidine interm. VII-4 described herein above, 0.94 g, 1.97 mmol) and ethyl-diisopropyl-amine (0.37 ml, 2.17 mmol) in CH$_2$Cl$_2$ (10 mL). The reaction was stirred over night, quenched by addition of an aqueous solution of NaHCO$_3$, and the product extracted with CH$_2$Cl$_2$. Purification by flash chromatography (SiO$_2$, EtOAc/Hx 1:1) yielded 0.83 g (70%) of rac-2-(3,5-bis-trifluoromethyl-phenyl)-N-[(3S,4R)-1-(2-bromo-acetyl)-4-(4-fluoro-phenyl)-pyrrolidin-3-yl]-N-methyl-isobutyramide as a white foam.
ES-MS m/e: 598.4 (M+H$^+$).

Example 1 rac-2-(3,5-Bis-trifluoromethyl-phenyl)-N-methyl-N-[(3S,4R)-1-(morpholine-4-carbonyl)-4-phenyl-pyrrolidin-3-yl]-isobutyramide

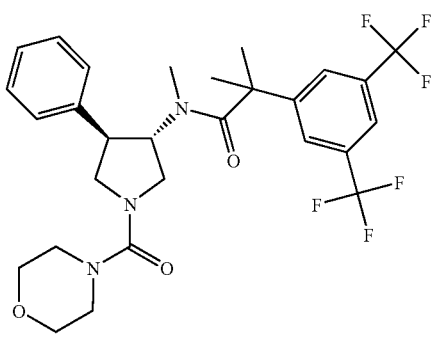

Coupling according to general procedure I:
Pyrrolidine intermediate: rac-2-(3,5-Bis-trifluoromethyl-phenyl)-N-methyl-N-((3S,4R)-4-phenyl-pyrrolidin-3-yl)-isobutyramide (VII-1),
Carbamoyl chloride: Morpholine-4-carbonyl chloride (commercially available),
ES-MS m/e: 572.1 (M+H$^+$).

Example 2 rac-2-(3,5-Bis-trifluoromethyl-phenyl)-N-[(3S,4R)-4-(4-chloro-phenyl)-1-(morpholine-4-carbonyl)-pyrrolidin-3-yl]-N-methyl-isobutyramide

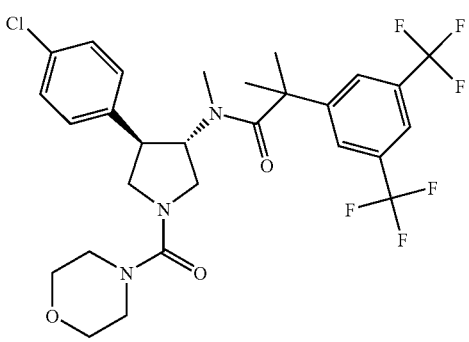

Coupling according to general procedure I:
Pyrrolidine intermediate: rac-2-(3,5-Bis-trifluoromethyl-phenyl)-N-[(3S,4R)-4-(4-chloro-phenyl)-pyrrolidin-3-yl]-N-methyl-isobutyramide (VII-2)
Carbamoyl chloride: Morpholine-4-carbonyl chloride (commercially available),
ES-MS m/e: 606.0 (M+H$^+$).

Example 3 rac-2-(3,5-Bis-trifluoromethyl-phenyl)-N-[(3S,4R)-4-(4-fluoro-phenyl)-1-(morpholine-4-carbonyl)-pyrrolidin-3-yl]-N-methyl-isobutyramide

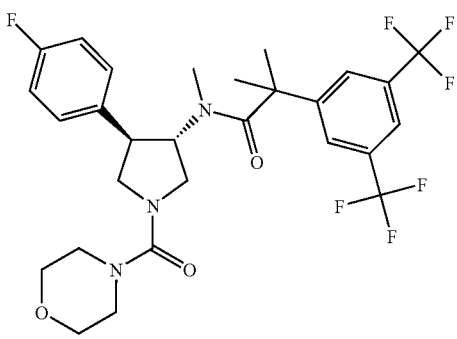

Coupling according to general procedure I:
Pyrrolidine intermediate: rac-2-(3,5-Bis-trifluoromethyl-phenyl)-N-[(3S,4R)-4-(4-fluoro-phenyl)-pyrrolidin-3-yl]-N-methyl-isobutyramide (VII-4)
Carbamoyl chloride: Morpholine-4-carbonyl chloride (commercially available),

Example 4 rac-2-(3,5-Bis-trifluoromethyl-phenyl)-N-[(3S,4R)-4-(4-chloro-phenyl)-1-cyclopropanecarbonyl-pyrrolidin-3-yl]-N-methyl-isobutyramide

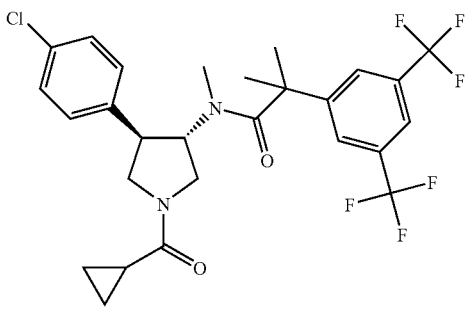

Coupling according to general procedure I:
Pyrrolidine intermediate: rac-2-(3,5-Bis-trifluoromethyl-phenyl)-N-[(3S,4R)-4-(4-chloro-phenyl)-pyrrolidin-3-yl]-N-methyl-isobutyramide (VII-2)
Acid chloride: Cyclopropanecarbonyl chloride (commercially available),
ES-MS m/e: 561.3 (M+H$^+$).

Example 5 rac-2-(3,5-Bis-trifluoromethyl-phenyl)-N-[(3S,4R)-4-(4-fluoro-phenyl)-1-(thiomorpholine-4-carbonyl)-pyrrolidin-3-yl]-N-methyl-isobutyramide

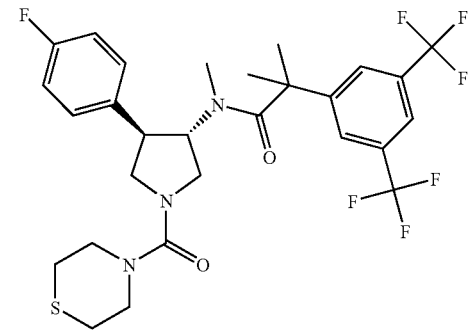

Coupling according to general procedure I:
Pyrrolidine intermediate: rac-2-(3,5-Bis-trifluoromethyl-phenyl)-N-[(3S,4R)-4-(4-fluoro-phenyl)-pyrrolidin-3-yl]-N-methyl-isobutyramide (VII-4)
Carbamoyl chloride: Thiomorpholine-4-carbonyl chloride (described in EP521827),
ES-MS m/e: 606.0 (M+H$^+$).

Example 6 rac-2-(3,5-Bis-trifluoromethyl-phenyl)-N-[(3S,4R)-1-(1,1-dioxo-1-thiomorpholine-4-carbonyl)-4-(4-fluoro-phenyl)-pyrrolidin-3-yl]-N-methyl-isobutyramide

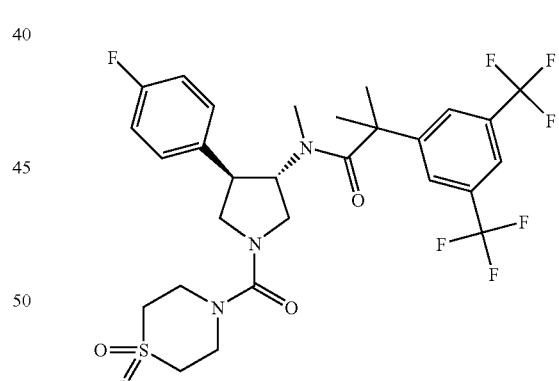

To a stirred solution of rac-2-(3,5-bis-trifluoromethyl-phenyl)-N-[(3S,4R)-4-(4-fluoro-phenyl)-1-(thiomorpholine-4-carbonyl)-pyrrolidin-3-yl]-N-methyl-isobutyramide (0.20 g, 0.33 mmol, described herein above) in MeOH (2 ml) at RT, was added potassium monopersulfate triple salt (0.30 g, 0.49 mmol). Stirring was continued an additional 3 hours, then a solution of NaHSO$_3$ (40%) was added, the ph was adjusted to 9 with an aqueous solution of NaHCO$_3$, and finally the product was extracted with Et$_2$O. Purification by flash chromatography (SiO$_2$, EtOAc/Hx 1:1) yielded 185 mg (88%) of the title compound as white foam.
ES-MS m/e: 638.2 (M+H$^+$).

Example 7 rac-2-(3,5-Bis-trifluoromethyl-phenyl)-N-[(3S,4R)-4-(4-fluoro-phenyl)-1-(4-methyl-piperazine-1-carbonyl)-pyrrolidin-3-yl]-N-methyl-isobutyramide

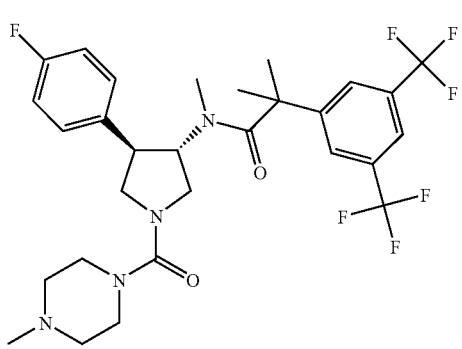

Coupling according to general procedure I:

Pyrrolidine intermediate: rac-2-(3,5-Bis-trifluoromethyl-phenyl)-N-[(3S,4R)-4-(4-fluoro-phenyl)-pyrrolidin-3-yl]-N-methyl-isobutyramide (VII-4)

Carbamoyl chloride: 4-Methyl-piperazine-1-carbonyl chloride (commercially available), ES-MS m/e: 603.2 (M+H$^+$).

Example 8 rac-(3S,4R)-3-{[2-(3,5-Bis-trifluoromethyl-phenyl)-2-methyl-propionyl]-methyl-amino}-4-(4-fluoro-phenyl)-pyrrolidine-1-carboxylic acid dimethylamide

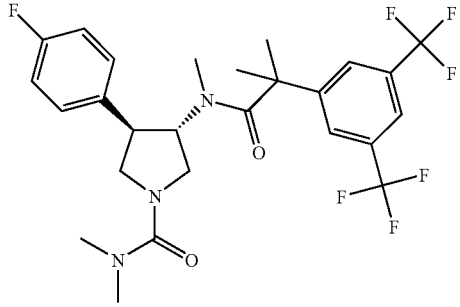

Coupling according to general procedure I:

Pyrrolidine intermediate: rac-2-(3,5-Bis-trifluoromethyl-phenyl)-N-[(3S,4R)-4-(4-fluoro-phenyl)-pyrrolidin-3-yl]-N-methyl-isobutyramide (VII-4)

Carbamoyl chloride: N,N-Dimethylcarbamyl chloride (commercially available),

ES-MS m/e: 548.3 (M+H$^+$).

Example 9 rac-2-(3,5-Bis-trifluoromethyl-phenyl)-N-[(3S,4R)-4-(4-fluoro-phenyl)-1-(pyrrolidine-1-carbonyl)-pyrrolidin-3-yl]-N-methyl-isobutyramide

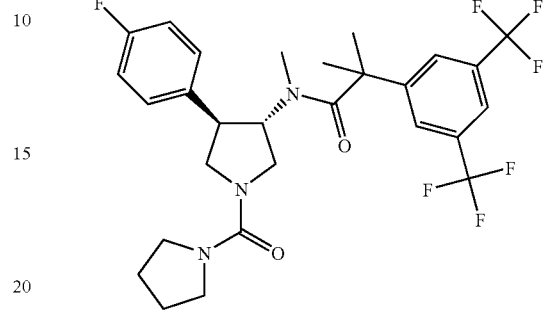

Coupling according to general procedure I:

Pyrrolidine intermediate: rac-2-(3,5-Bis-trifluoromethyl-phenyl)-N-[(3S,4R)-4-(4-fluoro-phenyl)-pyrrolidin-3-yl]-N-methyl-isobutyramide (VII-4)

Carbamoyl chloride: Pyrrolidine-1-carbonyl chloride (commercially available),

ES-MS m/e: 574.2 (M+H$^+$).

Example 10 rac-2-(3,5-Bis-trifluoromethyl-phenyl)-N-[(3S,4R)-1-[2-(1,1-dioxo-1-thiomorpholin-4-yl)-acetyl]-4-(4-fluoro-phenyl)-pyrrolidin-3-yl]-N-methyl-isobutyramide

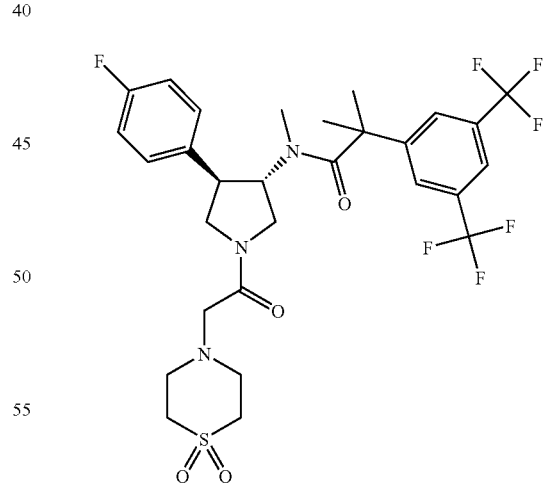

Coupling according to general procedure 3:

Pyrrolidine intermediate: rac-2-(3,5-Bis-trifluoromethyl-phenyl)-N-[(3S,4R)-1-(2-bromo-acetyl)-4-(4-fluoro-phenyl)-pyrrolidin-3-yl]-N-methyl-isobutyramide (IX-4)

Amine: Thiomorpholine 1,1-dioxide (commercially available),

ES-MS m/e: 652.1 (M+H$^+$).

Example 11 rac-2-(3,5-Bis-trifluoromethyl-phenyl)-N-[(3S,4R)-1-(2-cyclopropylamino-acetyl)-4-(4-fluoro-phenyl)-pyrrolidin-3-yl]-N-methyl-isobutyramide

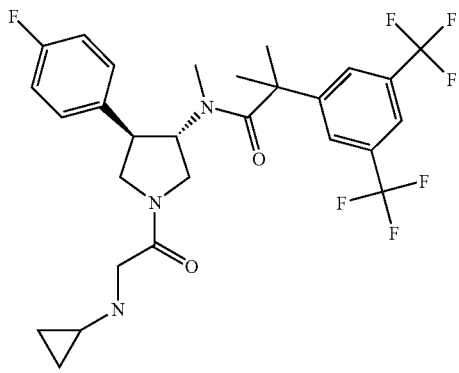

Coupling according to general procedure 3:

Pyrrolidine intermediate: rac-2-(3,5-Bis-trifluoromethyl-phenyl)-N-[(3S,4R)-1-(2-bromo-acetyl)-4-(4-fluoro-phenyl)-pyrrolidin-3-yl]-N-methyl-isobutyramide (IX-4)

Amine: Cyclopropylamine (commercially available),

ES-MS m/e: 574.2 (M+H$^+$).

Example 12 rac-2-(3,5-Bis-trifluoromethyl-phenyl)-N-[(3S,4R)-1-(2-dimethylamino-acetyl)-4-(4-fluoro-phenyl)-pyrrolidin-3-yl]-N-methyl-isobutyramide

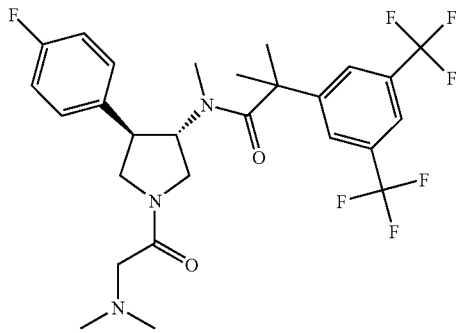

Coupling according to general procedure 3:

Pyrrolidine intermediate: rac-2-(3,5-Bis-trifluoromethyl-phenyl)-N-[(3S,4R)-1-(2-bromo-acetyl)-4-(4-fluoro-phenyl)-pyrrolidin-3-yl]-N-methyl-isobutyramide (IX-4)

Amine: Dimethyl-amine (commercially available),

ES-MS m/e: 562.3 (M+H$^+$).

Example 13 rac-2-(3,5-Bis-trifluoromethyl-phenyl)-N-{(3S,4R)-4-(4-fluoro-phenyl)-1-[2-(4-methanesulfonyl-piperazin-1-yl)-acetyl]-pyrrolidin-3-yl}-N-methyl-isobutyramide

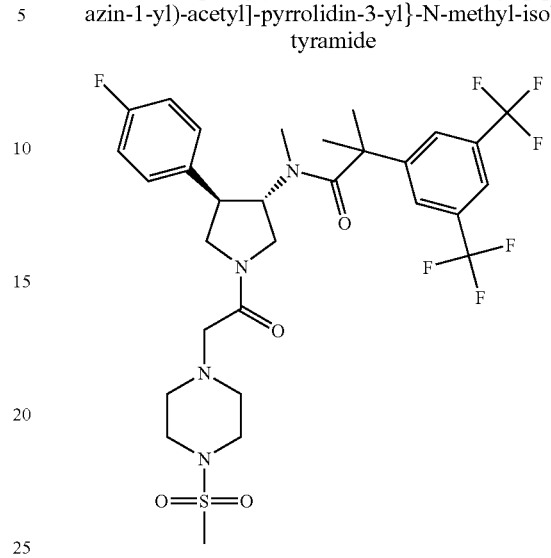

Coupling according to general procedure 3:

Pyrrolidine intermediate: rac-2-(3,5-Bis-trifluoromethyl-phenyl)-N-[(3S,4R)-1-(2-bromo-acetyl)-4-(4-fluoro-phenyl)-pyrrolidin-3-yl]-N-methyl-isobutyramide (IX-4)

Amine: 1-Methanesulfonyl-piperazine (commercially available),

ES-MS m/e: 681.3 (M+H$^+$).

Example 14 rac-N-[(3S,4R)-1-[2-(4-Acetyl-piperazin-1-yl)-acetyl]-4-(4-fluoro-phenyl)-pyrrolidin-3-yl]-2-(3,5-bis-trifluoromethyl-phenyl)-N-methyl-isobutyramide

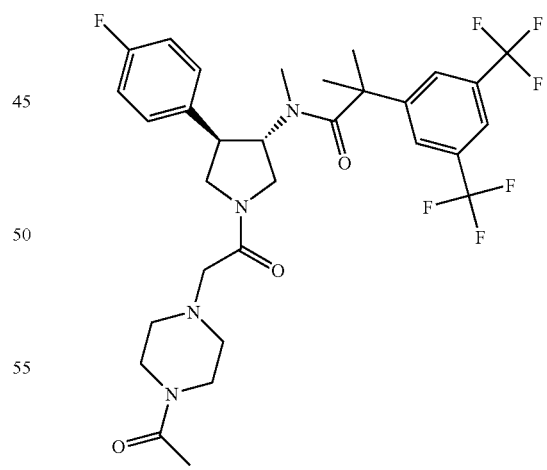

Coupling according to general procedure 3:

Pyrrolidine intermediate: rac-2-(3,5-Bis-trifluoromethyl-phenyl)-N-[(3S,4R)-1-(2-bromo-acetyl)-4-(4-fluoro-phenyl)-pyrrolidin-3-yl]-N-methyl-isobutyramide (IX-4)

Amine: 1-piperazin-1-yl-ethanone (commercially available),

ES-MS m/e: 645.4 (M+H$^+$).

Example 15 rac-2-(3,5-Bis-trifluoromethyl-phenyl)-N-[(3S,4R)-4-(4-fluoro-phenyl)-1-(4-methanesulfonyl-piperazine-1-carbonyl)-pyrrolidin-3-yl]-N-methyl-isobutyramide

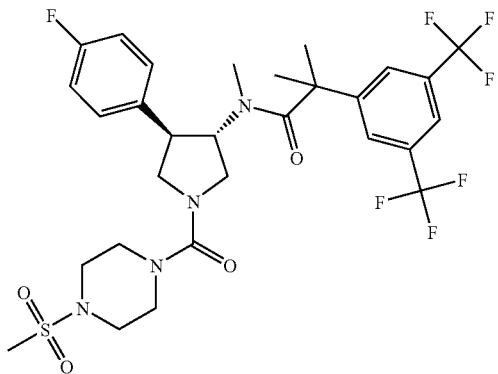

Coupling according to general procedure I:
Pyrrolidine intermediate: rac-2-(3,5-Bis-trifluoromethyl-phenyl)-N-[(3S,4R)-4-(4-fluoro-phenyl)-pyrrolidin-3-yl]-N-methyl-isobutyramide (VII-4)
Carbamoyl chloride: 4-Methanesulfonyl-piperazine-1-carbonyl chloride
ES-MS m/e: 667.3 (M+H$^+$).

4-Methanesulfonyl-piperazine-1-carbonyl chloride

To a stirred solution of carbonic acid ditrichloromethyl ester (triphosgene) (1.81 g, 6.09 mmol) in CH$_2$Cl$_2$ (30 ml) at 0° C., was added a solution of 1-methanesulfonyl-piperazine (2.0 g, 12.2 mmol) and pyridine (1.08 ml, 13.4 mmol) in CH$_2$Cl$_2$ (5 ml) over 30 minutes. The temperature was raised to RT, and stirring was continued over night. The organic phase was washed with H$_2$O, dried over Na$_2$SO$_4$. Purification by flash chromatography (SiO$_2$, EtOAc) yielded 2.20 g (79%) of the title compound as white solid.

Example 16 rac-N-[(3S,4R)-1-(4-Acetyl-piperazine-1-carbonyl)-4-(4-fluoro-phenyl)-pyrrolidin-3-yl]-2-(3,5-bis-trifluoromethyl-phenyl)-N-methyl-isobutyramide

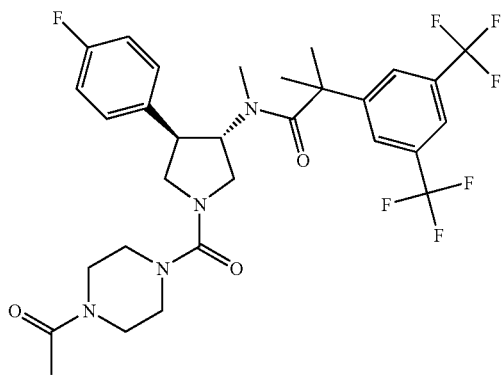

Coupling according to general procedure I:
Pyrrolidine intermediate: rac-2-(3,5-Bis-trifluoromethyl-phenyl)-N-[(3S,4R)-4-(4-fluoro-phenyl)-pyrrolidin-3-yl]-N-methyl-isobutyramide (VII-4)
Carbamoyl chloride: 4-Acetyl-piperazine-1-carbonyl chloride
ES-MS m/e: 631.5 (M+H$^+$).

4-Acetyl-piperazine-1-carbonyl chloride

To a stirred solution of carbonic acid ditrichloromethyl ester (triphosgene) (2.31 g, 7.80 mmol) in CH$_2$Cl$_2$ (30 ml) at 0° C., was added a solution of 1-piperazin-1-yl-ethanone (2.0 g, 15.6 mmol) and pyridine (1.38 ml, 17.2 mmol) in CH$_2$Cl$_2$ (5 ml) over 30 minutes. The temperature was raised to RT, and stirring was continued over night. The organic phase was washed with H$_2$O, dried over Na$_2$SO$_4$. Purification by flash chromatography (SiO$_2$, EtOAc) yielded 1.12 g (38%) of the title compound as white solid.

Example 17 rac-2-(3,5-Bis-trifluoromethyl-phenyl)-N-[(3S,4R)-4-(4-fluoro-phenyl)-1-(2-morpholin-4-yl-acetyl)-pyrrolidin-3-yl]-N-methyl-isobutyramide

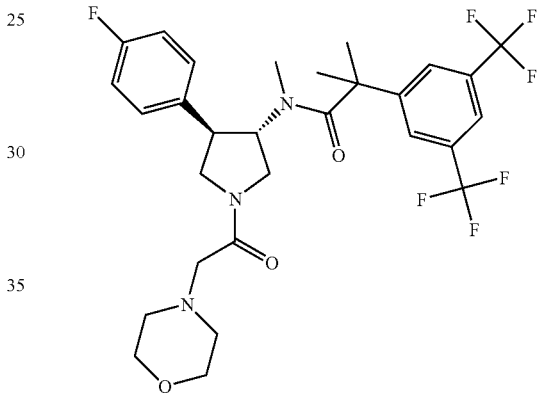

Coupling according to general procedure 3:
Pyrrolidine intermediate: rac-2-(3,5-Bis-trifluoromethyl-phenyl)-N-[(3S,4R)-1-(2-bromo-acetyl)-4-(4-fluoro-phenyl)-pyrrolidin-3-yl]-N-methyl-isobutyramide (IX-4)
Amine: Morpholine (commercially available),
ES-MS m/e: 604.3 (M+H$^+$).

Example 18 rac-4-[(3S,4R)-3-{[2-(3,5-Bis-trifluoromethyl-phenyl)-2-methyl-propionyl]-methyl-amino}-4-(4-fluoro-phenyl)-pyrrolidine-1-carbonyl]-piperazine-1-carboxylic acid tert-butyl ester

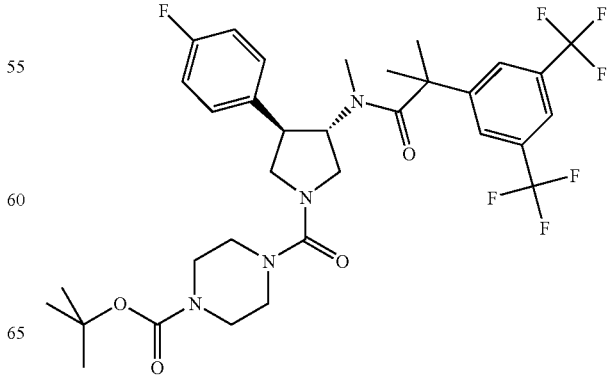

Coupling according to general procedure I:
Pyrrolidine intermediate: rac-2-(3,5-Bis-trifluoromethyl-phenyl)-N-[(3S,4R)-4-(4-fluoro-phenyl)-pyrrolidin-3-yl]-N-methyl-isobutyramide (VII-4)
Carbamoyl chloride: 4-Chlorocarbonyl-piperazine-1-carboxylic acid tert-butyl ester (commercially available)
ES-MS m/e: 689.3 (M+H⁺).

Example 19 rac-2-(3,5-Bis-trifluoromethyl-phenyl)-N-[(3S,4R)-4-(4-fluoro-phenyl)-1-(piperazine-1-carbonyl)-pyrrolidin-3-yl]-N-methyl-isobutyramide

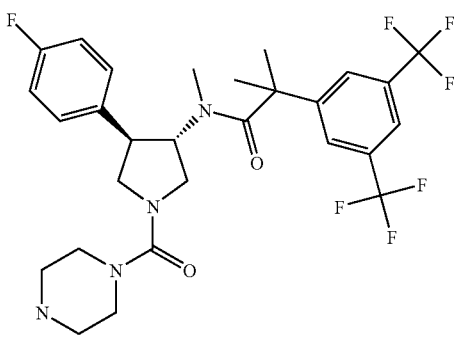

To a stirred solution of rac-4-[(3S,4R)-3-{[2-(3,5-Bis-trifluoromethyl-phenyl)-2-methyl-propionyl]-methyl-amino}-4-(4-fluoro-phenyl)-pyrrolidine-1-carbonyl]-piperazine-1-carboxylic acid tert-butyl ester (21 mg, 0.30 mmol) in CH$_2$Cl$_2$ (4 ml) at RT, was added TFA (1 ml). After 1 hour, the reaction mixture was neutralized by addition of an aqueous solution of NaHCO$_3$. The organic phases were dried over Na$_2$SO$_4$ to yield the title compound as a white solid.
ES-MS m/e: 589.5 (M+H⁺).

Example 20 rac-N-[(3S,4R)-1-(1-Acetyl-piperidine-4-carbonyl)-4-(4-fluoro-phenyl)-pyrrolidin-3-yl]-2-(3,5-bis-trifluoromethyl-phenyl)-N-methyl-isobutyramide

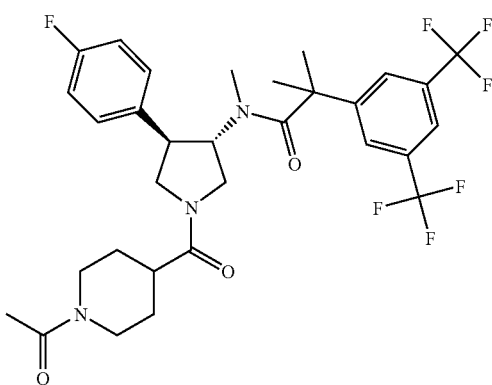

Coupling according to general procedure I:
Pyrrolidine intermediate: rac-2-(3,5-Bis-trifluoromethyl-phenyl)-N-[(3S,4R)-4-(4-fluoro-phenyl)-pyrrolidin-3-yl]-N-methyl-isobutyramide (VII-4)

Acid chloride: 1-Acetyl-piperidine-4-carbonyl chloride (commercially available)
ES-MS m/e: 630.5 (M+H⁺).

Example 21 rac-(3S,4R)-3-{[2-(3,5-Bis-trifluoromethyl-phenyl)-2-methyl-propionyl]-methyl-amino}-4-(4-fluoro-phenyl)-pyrrolidine-1-carboxylic acid bis-(2-hydroxy-ethyl)-amide

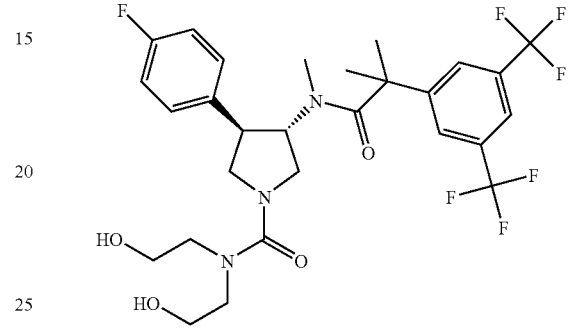

Coupling according to general procedure II:
Pyrrolidine intermediate: rac-(3S,4R)-3-{[2-(3,5-Bis-trifluoromethyl-phenyl)-2-methyl-propionyl]-methyl-amino}-4-(4-fluoro-phenyl)-pyrrolidine-1-carbonyl chloride (VIII-4)
Amine: 2-(2-Hydroxy-ethylamino)-ethanol (commercially available).
ES-MS m/e: 608.3 (M+H⁺).

Example 22 rac-2-(3,5-Bis-trifluoromethyl-phenyl)-N-[(3S,4R)-1-(4-methanesulfonyl-piperazine-1-carbonyl)-4-phenyl-pyrrolidin-3-yl]-N-methyl-isobutyramide

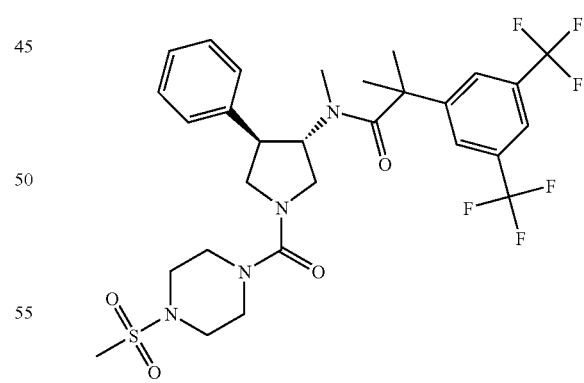

Coupling according to general procedure I:
Pyrrolidine intermediate: rac-2-(3,5-Bis-trifluoromethyl-phenyl)-N-[(3S,4R)-1-(4-methanesulfonyl-piperazine-1-carbonyl)-4-phenyl-pyrrolidin-3-yl]-N-methyl-isobutyramide (VII-1)
Carbamoyl chloride: 4-Methanesulfonyl-piperazine-1-carbonyl chloride (described herein above)
ES-MS m/e: 649.5 (M+H⁺).

Example 23 rac-2-(3,5-Dichloro-phenyl)-N-[(3S,4R)-4-(4-fluoro-phenyl)-1-(4-methanesulfonyl-piperazine-1-carbonyl)-pyrrolidin-3-yl]-N-methyl-isobutyramide

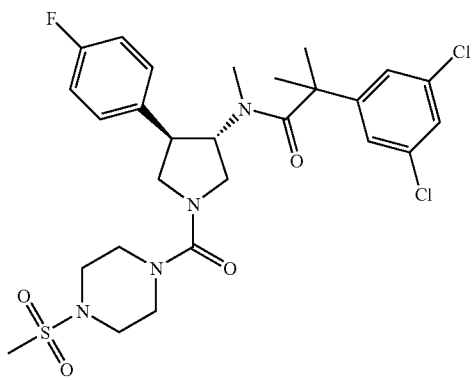

Coupling according to general procedure I:
Pyrrolidine intermediate: rac-2-(3,5-Dichloro-phenyl)-N-[(3S,4R)-4-(4-fluoro-phenyl)-pyrrolidin-3-yl]-N-methyl-isobutyramide (VII-5)
Carbamoyl chloride: 4-Methanesulfonyl-piperazine-1-carbonyl chloride (described herein above)
ES-MS m/e: 599.2 (M+H$^+$).

Example 24 rac-2-(3,5-Dichloro-phenyl)-N-[(3S,4R)-4-(4-fluoro-phenyl)-1-(morpholine-4-carbonyl)-pyrrolidin-3-yl]-N-methyl-isobutyramide

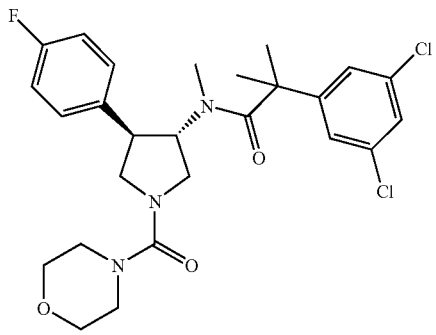

Coupling according to general procedure I:
Pyrrolidine intermediate: rac-2-(3,5-Dichloro-phenyl)-N-[(3S,4R)-4-(4-fluoro-phenyl)-pyrrolidin-3-yl]-N-methyl-isobutyramide (VII-5)
Carbamoyl chloride: Morpholine-4-carbonyl chloride (commercially available)
ES-MS m/e: 522.3 (M+H$^+$).

Example 25 rac-2-(3,5-Bis-trifluoromethyl-phenyl)-N-[(3S,4R)-4-(4-fluoro-phenyl)-1-(4-oxo-cyclohexanecarbonyl)-pyrrolidin-3-yl]-N-methyl-isobutyramide

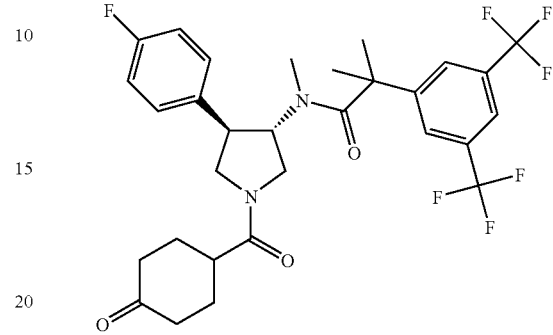

Coupling according to general procedure I:
Pyrrolidine intermediate: rac-2-(3,5-Bis-trifluoromethyl-phenyl)-N-[(3S,4R)-4-(4-fluoro-phenyl)-pyrrolidin-3-yl]-N-methyl-isobutyramide (VII-4)
Acid chloride: 4-Oxo-cyclohexanecarbonyl chloride
ES-MS m/e: 601.5 (M+H$^+$).

4-Oxo-cyclohexanecarbonyl chloride

To a stirred solution of 4-oxo-cyclohexanecarboxylic acid (commercially available) (115 mg, 0.81 mmol) in CH$_2$Cl$_2$ (3 ml) was added oxalyl chloride (205 mg, 1.61 mmol). The reaction mixture was stirred at RT over night, and then concentrated under vacuo. The product was used directly in the next step without further purification.

Example 26 rac-(3S,4R)-3-{[2-(3,5-Bis-trifluoromethyl-phenyl)-2-methyl-propionyl]-methyl-amino}-4-(4-fluoro-phenyl)-pyrrolidine-1-carboxylic acid (2-hydroxy-ethyl)-amide

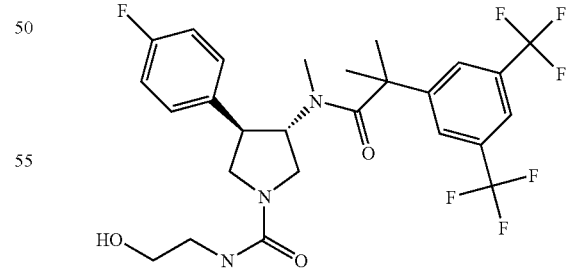

Coupling according to general procedure II:
Pyrrolidine intermediate: rac-(3S,4R)-3-{[2-(3,5-Bis-trifluoromethyl-phenyl)-2-methyl-propionyl]-methyl-amino}-4-(4-fluoro-phenyl)-pyrrolidine-1-carbonyl chloride (VIII-4)
Amine: 2-Amino-ethanol (commercially available).
ES-MS m/e: 564.3 (M+H$^+$).

Example 27 rac-2-(3,5-Bis-trifluoromethyl-phenyl)-N-[(3S,4R)-4-(4-fluoro-2-methyl-phenyl)-1-(morpholine-4-carbonyl)-pyrrolidin-3-yl]-N-methyl-isobutyramide

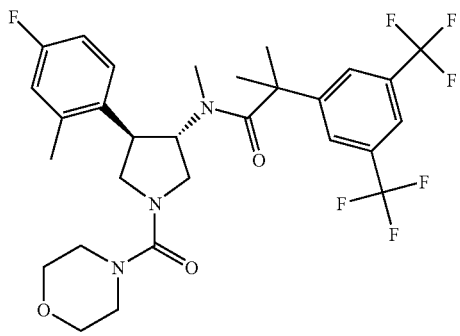

Coupling according to general procedure I:

Pyrrolidine intermediate: rac-2-(3,5-Bis-trifluoromethyl-phenyl)-N-[(3S,4R)-4-(4-fluoro-2-methyl-phenyl)-pyrrolidin-3-yl]-N-methyl-isobutyramide (VII-7)

Carbamoyl chloride: Morpholine-4-carbonyl chloride (commercially available)

ES-MS m/e: 604.5 (M+H$^+$).

Example 28 rac-2-(3,5-Bis-trifluoromethyl-phenyl)-N-[(3S,4R)-4-(4-fluoro-2-methyl-phenyl)-1-(4-methanesulfonyl-piperazine-1-carbonyl)-pyrrolidin-3-yl]-N-methyl-isobutyramide

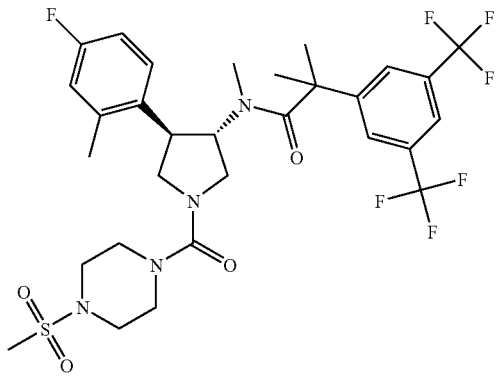

Coupling according to general procedure I:

Pyrrolidine intermediate: rac-2-(3,5-Bis-trifluoromethyl-phenyl)-N-[(3S,4R)-4-(4-fluoro-2-methyl-phenyl)-pyrrolidin-3-yl]-N-methyl-isobutyramide (VII-7)

Carbamoyl chloride: 4-Methanesulfonyl-piperazine-1-carbonyl chloride (described herein above).

ES-MS m/e: 681.5 (M+H$^+$).

Example 29 rac-2-(3,5-Bis-trifluoromethyl-phenyl)-N-[(3S,4R)-1-(3-hydroxy-azetidine-1-carbonyl)-4-phenyl-pyrrolidin-3-yl]-N-methyl-isobutyramide

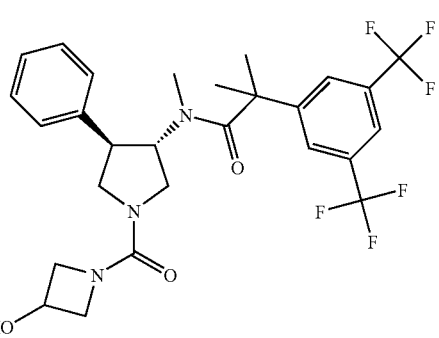

Coupling according to general procedure II:

Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)

Amine: Azetidin-3-ol (commercially available).

ES-MS m/e: 558.2 (M+H$^+$).

Example 30 rac-2-(3,5-Bis-trifluoromethyl-phenyl)-N-[(3S,4R)-1-(4-hydroxy-piperidine-1-carbonyl)-4-phenyl-pyrrolidin-3-yl]-N-methyl-isobutyramide

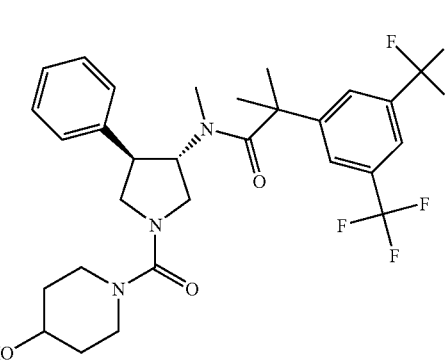

Coupling according to general procedure II:

Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)

Amine: Piperidin-4-ol (commercially available).

ES-MS m/e: 586.5 (M+H$^+$).

Example 31 rac-(3S,4R)-3-{[2-(3,5-Bis-trifluoromethyl-phenyl)-2-methyl-propionyl]-methyl-amino}-4-phenyl-pyrrolidine-1-carboxylic acid (2-hydroxy-ethyl)-methyl-amide

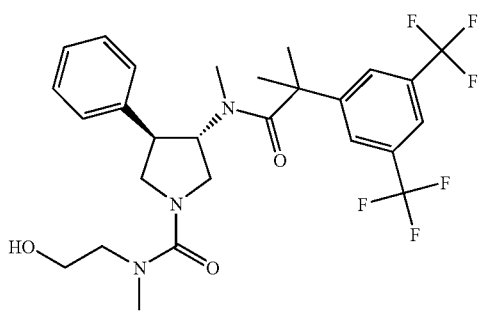

Coupling according to general procedure II:
Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)
Amine: 2-Methylamino-ethanol (commercially available).
ES-MS m/e: 560.5 (M+H$^+$).

Example 32 rac-(3S,4R)-3-{[2-(3,5-Bis-trifluoromethyl-phenyl)-2-methyl-propionyl]-methyl-amino}-4-phenyl-pyrrolidine-1-carboxylic acid (2-methoxy-ethyl)-amide

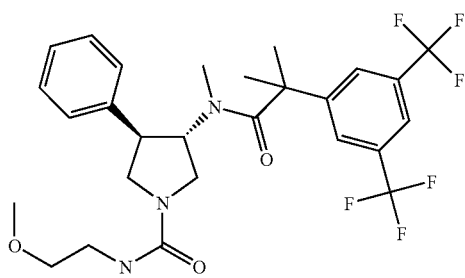

Coupling according to general procedure II:
Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)
Amine: 2-Methoxy-ethylamine (commercially available).
ES-MS m/e: 560.3 (M+H$^+$).

Example 33 rac-(3S,4R)-3-{[2-(3,5-Bis-trifluoromethyl-phenyl)-2-methyl-propionyl]-methyl-amino}-4-phenyl-pyrrolidine-1-carboxylic acid (2-hydroxy-1-hydroxymethyl-ethyl)-amide

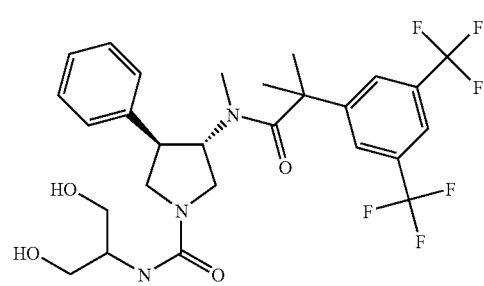

Coupling according to general procedure II:
Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)
Amine: 2-Amino-propane-1,3-diol (commercially available).
ES-MS m/e: 576.7 (M+H$^+$).

Example 34 rac-(3S,4R)-3-{[2-(3,5-Bis-trifluoromethyl-phenyl)-2-methyl-propionyl]-methyl-amino}-4-phenyl-pyrrolidine-1-carboxylic acid (3-hydroxy-propyl)-amide

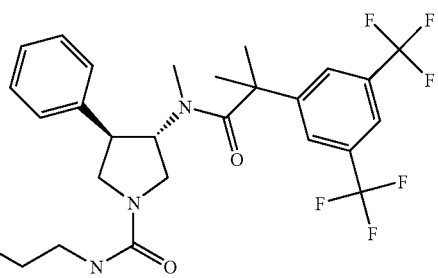

Coupling according to general procedure II:
Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)
Amine: 3-Amino-propan-1-ol (commercially available).
ES-MS m/e: 560.5 (M+H$^+$).

Example 35 rac-(3S,4R)-3-{[2-(3,5-Bis-trifluoromethyl-phenyl)-2-methyl-propionyl]-methyl-amino}-4-phenyl-pyrrolidine-1-carboxylic acid [2-(2-hydroxy-ethoxy)-ethyl]-amide

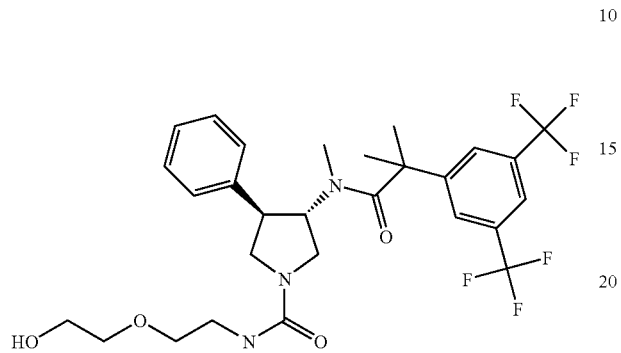

Coupling according to general procedure II:

Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)

Amine: 2-(2-Amino-ethoxy)-ethanol (commercially available).

ES-MS m/e: 590.7 (M+H$^+$).

Example 36 rac-(3S,4R)-3-{[2-(3,5-Bis-trifluoromethyl-phenyl)-2-methyl-propionyl]-methyl-amino}-4-phenyl-pyrrolidine-1-carboxylic acid (2-hydroxy-1,1-dimethyl-ethyl)-amide

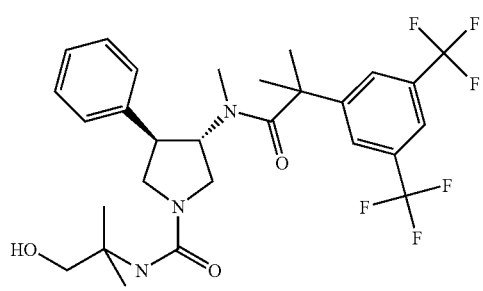

Coupling according to general procedure II:

Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)

Amine: 2-Amino-2-methyl-propan-1-ol (commercially available).

ES-MS m/e: 574.5 (M+H$^+$).

Example 37 rac-2-(3,5-Bis-trifluoromethyl-phenyl)-N-methyl-N-[(3S,4R)-1-(morpholine-4-carbonyl)-4-o-tolyl-pyrrolidin-3-yl]-isobutyramide

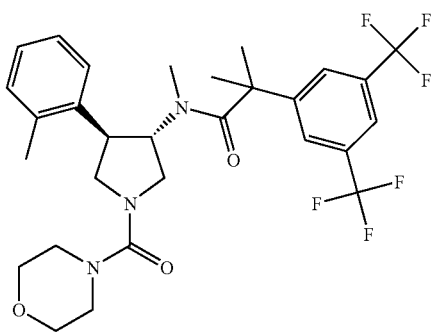

Coupling according to general procedure I:

Pyrrolidine intermediate: rac-2-(3,5-Bis-trifluoromethyl-phenyl)-N-methyl-N-((3S,4R)-4-o-tolyl-pyrrolidin-3-yl)-isobutyramide (VII-8)

Carbamoyl chloride: Morpholine-4-carbonyl chloride (commercially available)

ES-MS m/e: 586.5 (M+H$^+$).

Example 38 rac-2-(3,5-Bis-trifluoromethyl-phenyl)-N-[(3S,4R)-1-(4-methanesulfonyl-piperazine-1-carbonyl)-4-o-tolyl-pyrrolidin-3-yl]-N-methyl-isobutyramide

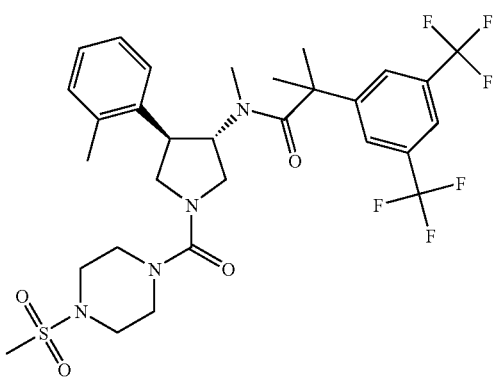

Coupling according to general procedure I:

Pyrrolidine intermediate: rac-2-(3,5-Bis-trifluoromethyl-phenyl)-N-methyl-N-((3S,4R)-4-o-tolyl-pyrrolidin-3-yl)-isobutyramide (VII-8)

Carbamoyl chloride: 4-Methanesulfonyl-piperazine-1-carbonyl chloride (described herein above).

ES-MS m/e: 663.3 (M+H$^+$).

Example 39 rac-2-(3,5-Dichloro-phenyl)-N-methyl-N-[(3S,4R)-1-(morpholine-4-carbonyl)-4-o-tolyl-pyrrolidin-3-yl]-isobutyramide

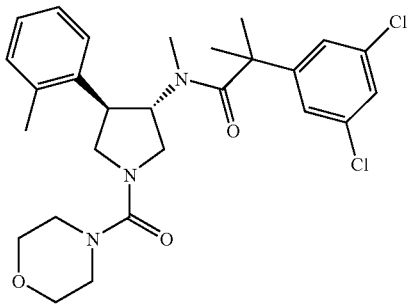

Coupling according to general procedure I:

Pyrrolidine intermediate: rac-2-(3,5-Dichloro-phenyl)-N-methyl-N-((3S,4R)-4-o-tolyl-pyrrolidin-3-yl)-isobutyramide (VII-9)

Carbamoyl chloride: Morpholine-4-carbonyl chloride (commercially available)

ES-MS m/e: 518.5 (M+H$^+$).

Example 40 rac-2-(3,5-Dichloro-phenyl)-N-[(3S,4R)-1-(4-methanesulfonyl-piperazine-1-carbonyl)-4-o-tolyl-pyrrolidin-3-yl]-N-methyl-isobutyramide

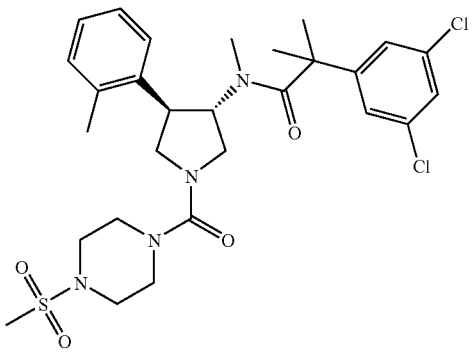

Coupling according to general procedure I:

Pyrrolidine intermediate: rac-2-(3,5-Dichloro-phenyl)-N-methyl-N-((3S,4R)-4-o-tolyl-pyrrolidin-3-yl)-isobutyramide (VII-9)

Carbamoyl chloride: 4-Methanesulfonyl-piperazine-1-carbonyl chloride (described herein above).

ES-MS m/e: 597.1 (M+H$^+$).

Example 41 rac-2-(3-Chloro-phenyl)-N-[(3S,4R)-4-(4-fluoro-phenyl)-1-(4-methanesulfonyl-piperazine-1-carbonyl)-pyrrolidin-3-yl]-N-methyl-isobutyramide

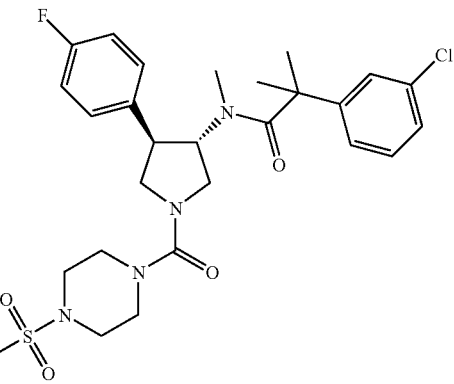

Coupling according to general procedure I:

Pyrrolidine intermediate: rac-2-(3-Chloro-phenyl)-N-[(3S,4R)-4-(4-fluoro-phenyl)-pyrrolidin-3-yl]-N-methyl-isobutyramide (VII-6)

Carbamoyl chloride: 4-Methanesulfonyl-piperazine-1-carbonyl chloride (described herein above).

ES-MS m/e: 565.3 (M+H$^+$).

Example 42

(3S,4R)-3-{[2-(3,5-Bis-trifluoromethyl-phenyl)-2-methyl-propionyl]-methyl-amino}-4-phenyl-pyrrolidine-1-carboxylic acid ((S)-1-hydroxymethyl-3-methylsulfanyl-propyl)-amide

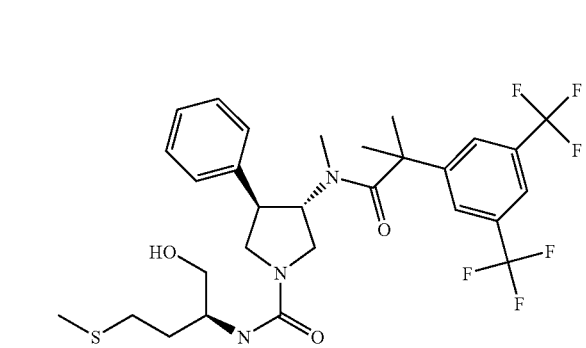

Coupling according to general procedure II:

Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)

Amine: (S)-2-Amino-4-methylsulfanyl-butan-1-ol (L-Methioninol, commercially available).

ES-MS m/e: 620.3 (M+H$^+$).

Example 43

(3S,4R)-3-{[2-(3,5-Bis-trifluoromethyl-phenyl)-2-methyl-propionyl]-methyl-amino}-4-phenyl-pyrrolidine-1-carboxylic acid ((S)-1-hydroxymethyl-3-methyl-butyl)-amide

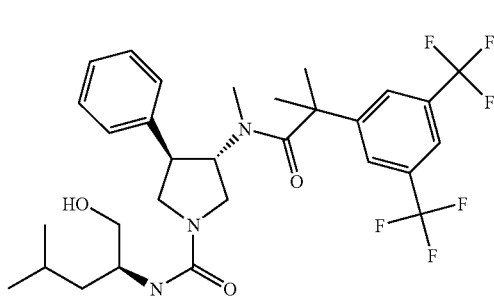

Coupling according to general procedure II:

Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)

Amine: (S)-2-Amino-4-methyl-pentan-1-ol (L-leucinol, commercially available).

ES-MS m/e: 602.5 (M+H$^+$).

Example 44

(3S,4R)-3-{[2-(3,5-Bis-trifluoromethyl-phenyl)-2-methyl-propionyl]-methyl-amino}-4-phenyl-pyrrolidine-1-carboxylic acid ((R)-2-hydroxy-1-methyl-ethyl)-amide

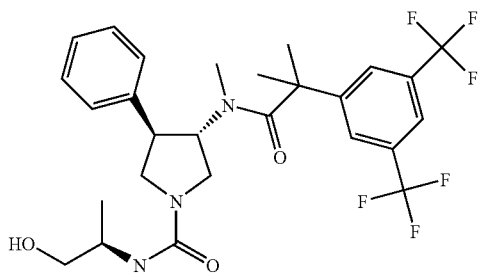

Coupling according to general procedure II:

Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)

Amine: (R)-2-Amino-propan-1-ol (D-alaninol, commercially available).

ES-MS m/e: 560.5 (M+H$^+$).

Example 45

(3S,4R)-3-{[2-(3,5-Bis-trifluoromethyl-phenyl)-2-methyl-propionyl]-methyl-amino}-4-phenyl-pyrrolidine-1-carboxylic acid ((S)-1-hydroxymethyl-2-methyl-propyl)-amide

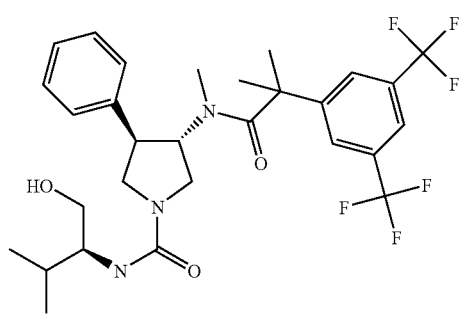

Coupling according to general procedure II:

Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)

Amine: (S)-2-Amino-3-methyl-butan-1-ol (L-valinol, commercially available).

ES-MS m/e: 588.5 (M+H$^+$).

Example 46

(3S,4R)-3-{[2-(3,5-Bis-trifluoromethyl-phenyl)-2-methyl-propionyl]-methyl-amino}-4-phenyl-pyrrolidine-1-carboxylic acid ((S)-2-hydroxy-propyl)-amide

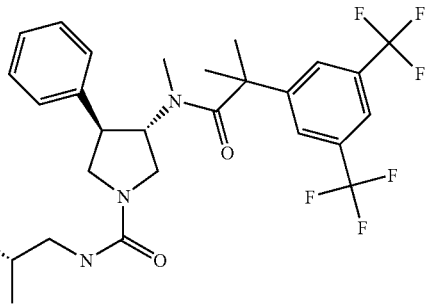

Coupling according to general procedure II:

Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)

Amine: (S)-1-Amino-propan-2-ol (commercially available).

ES-MS m/e: 560.3 (M+H$^+$).

Example 47

2-(3,5-Bis-trifluoromethyl-phenyl)-N-[((3S,4R)-1-((S)-2-hydroxymethyl-pyrrolidine-1-carbonyl)-4-phenyl-pyrrolidin-3-yl]-N-methyl-isobutyramide

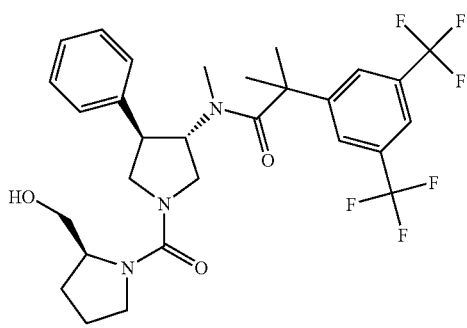

Coupling according to general procedure II:

Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)

Amine: (S)-1-Pyrrolidin-2-yl-methanol (commercially available).

ES-MS m/e: 586.5 (M+H$^+$).

Example 48

(3S,4R)-3-{[2-(3,5-Bis-trifluoromethyl-phenyl)-2-methyl-propionyl]-methyl-amino}-4-phenyl-pyrrolidine-1-carboxylic acid ((R)-2-hydroxy-propyl)-amide

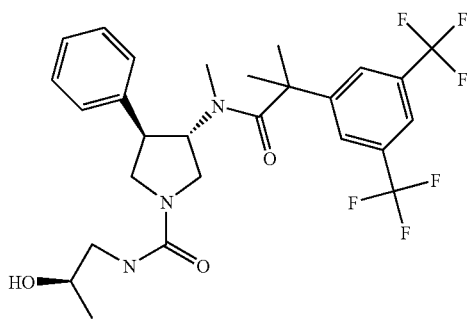

Coupling according to general procedure II:

Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)

Amine: (R)-1-Amino-propan-2-ol (commercially available).

ES-MS m/e: 560.5 (M+H$^+$).

Example 49

2-(3,5-Bis-trifluoromethyl-phenyl)-N-[(3S,4R)-1-((2R,3S)-3-hydroxy-2-hydroxymethyl-pyrrolidine-1-carbonyl)-4-phenyl-pyrrolidin-3-yl]-N-methyl-isobutyramide

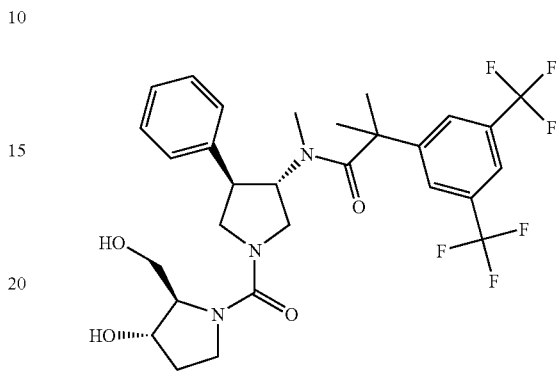

Coupling according to general procedure II:

Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)

Amine: (2R,3S)-2-Hydroxymethyl-pyrrolidin-3-ol (described in *J. Org. Chem.* 1989, 54(20), 4812).

ES-MS m/e: 602.3 (M+H$^+$).

Example 50

2-(3,5-Bis-trifluoromethyl-phenyl)-N-[(3S,4R)-1-((S)-3-hydroxy-pyrrolidine-1-carbonyl)-4-phenyl-pyrrolidin-3-yl]-N-methyl-isobutyramide

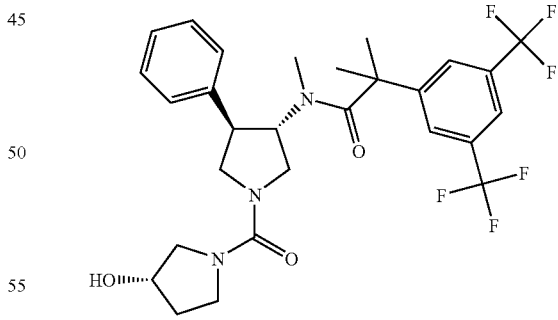

Coupling according to general procedure II:

Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)

Amine: (S)-Pyrrolidin-3-ol (described in WO2007011162).

ES-MS m/e: 572.3 (M+H$^+$).

Example 51

2-(3,5-Bis-trifluoromethyl-phenyl)-N-[(3S,4R)-1-((S)-2-methoxymethyl-pyrrolidine-1-carbonyl)-4-phenyl-pyrrolidin-3-yl]-N-methyl-isobutyramide

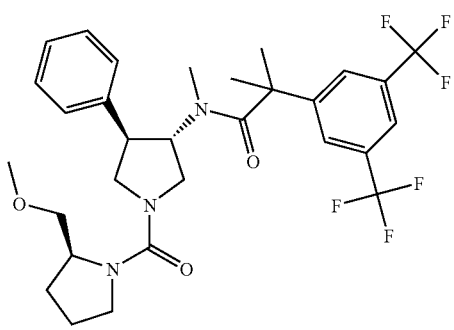

Coupling according to general procedure II:

Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)

Amine: (S)-2-Methoxymethyl-pyrrolidine (commercially available).

ES-MS m/e: 600.3 (M+H$^+$).

Example 52

N-[(3S,4R)-1-((R)-3-Acetylamino-pyrrolidine-1-carbonyl)-4-phenyl-pyrrolidin-3-yl]-2-(3,5-bis-trifluoromethyl-phenyl)-N-methyl-isobutyramide

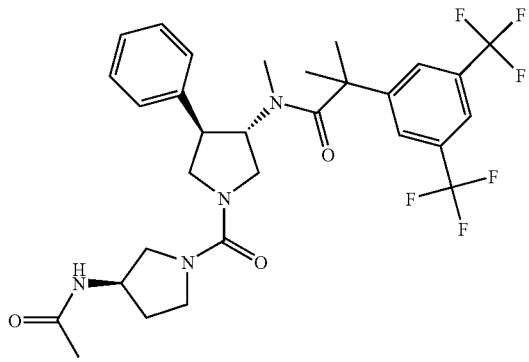

Coupling according to general procedure II:

Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)

Amine: (R)—N-Pyrrolidin-3-yl-acetamide (commercially available).

ES-MS m/e: 613.3 (M+H$^+$).

Example 53 rac-(3S,4R)-3-{[2-(3,5-Dichloro-phenyl)-2-methyl-propionyl]-methyl-amino}-4-(4-fluoro-phenyl)-pyrrolidine-1-carboxylic acid (3-hydroxy-propyl)-amide

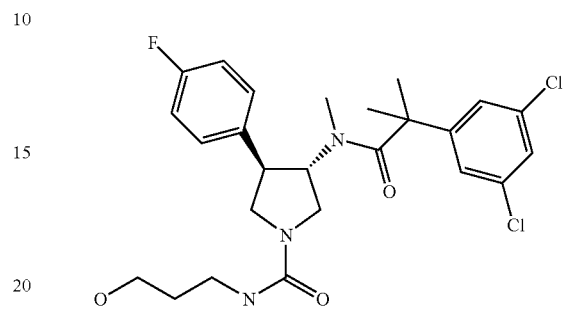

Coupling according to general procedure II:

Pyrrolidine intermediate: rac-(3S,4R)-3-{[2-(3,5-Dichloro-phenyl)-2-methyl-propionyl]-methyl-amino}-4-(4-fluoro-phenyl)-pyrrolidine-1-carbonyl chloride (VIII-5)

Amine: 3-Amino-propan-1-ol (commercially available).

ES-MS m/e: 510.3 (M+H$^+$).

Example 54 rac-(3S,4R)-3-{[2-(3,5-Dichloro-phenyl)-2-methyl-propionyl]-methyl-amino}-4-(4-fluoro-phenyl)-pyrrolidine-1-carboxylic acid bis-(2-hydroxy-ethyl)-amide

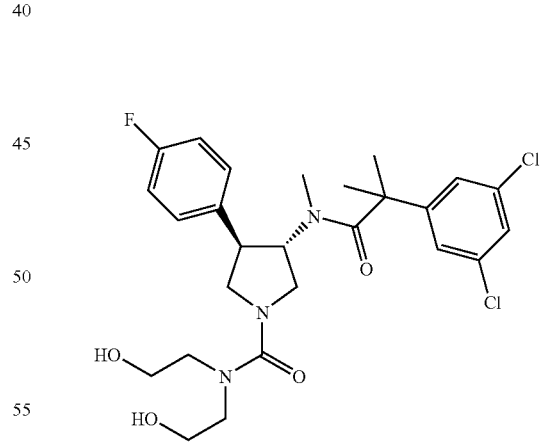

Coupling according to general procedure II:

Pyrrolidine intermediate: rac-(3S,4R)-3-{[2-(3,5-Dichloro-phenyl)-2-methyl-propionyl]-methyl-amino}-4-(4-fluoro-phenyl)-pyrrolidine-1-carbonyl chloride (VIII-5)

Amine: 2-(2-Hydroxy-ethylamino)-ethanol (commercially available).

ES-MS m/e: 540.3 (M+H$^+$).

Example 55 rac-N-[(3S,4R)-4-(4-Chloro-phenyl)-1-(4-methane-sulfonyl-piperazine-1-carbonyl)-pyrrolidin-3-yl]-2-(3,5-dichloro-phenyl)-N-methyl-isobutyramide

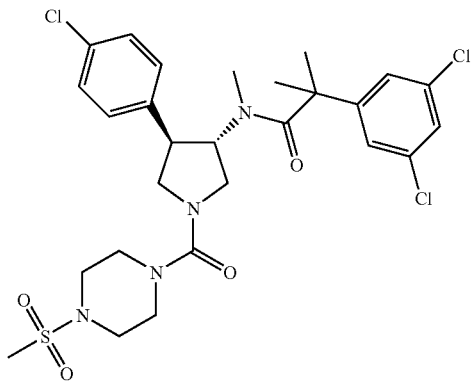

Coupling according to general procedure I:

Pyrrolidine intermediate: rac-N-[(3S,4R)-4-(4-Chloro-phenyl)-pyrrolidin-3-yl]-2-(3,5-dichloro-phenyl)-N-methyl-isobutyramide (VII-3)

Carbamoyl chloride: 4-Methanesulfonyl-piperazine-1-carbonyl chloride (described herein above)

ES-MS m/e: 617.3 (M+H$^+$).

Example 56

2-(3,5-Bis-trifluoromethyl-phenyl)-N-methyl-N-[(3S,4R)-4-phenyl-1-((R)-tetrahydro-furan-2-carbonyl)-pyrrolidin-3-yl]-isobutyramide

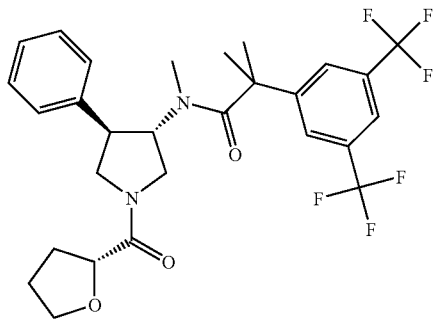

To a stirred solution of (R)-tetrahydro-furan-2-carboxylic acid (described in *Tetrahedron Asymmetry*, 2003, 14(10, 1385) (5.0 mg, 0.043 mmol) in THF (2 ml) at RT were added Et$_3$N (12 µl, 0.086 mmol), BOP (25 mg, 0.057 mmol) and rac-2-(3,5-bis-trifluoromethyl-phenyl)-N-methyl-N-((3S,4R)-4-phenyl-pyrrolidin-3-yl)-isobutyramide (Intermediate VII-1) (20 mg, 0.043 mmol). Stirring was continued at 40° C. for 48 hours. Concentration and purification by preparative HPLC afforded 5.8 mg (28%) of the title compound.

ES-MS m/e: 557.2 (M+H$^+$).

Example 57

2-(3,5-Bis-trifluoromethyl-phenyl)-N-methyl-N-[(3S,4R)-4-phenyl-1-((S)-tetrahydro-furan-2-carbonyl)-pyrrolidin-3-yl]-isobutyramide

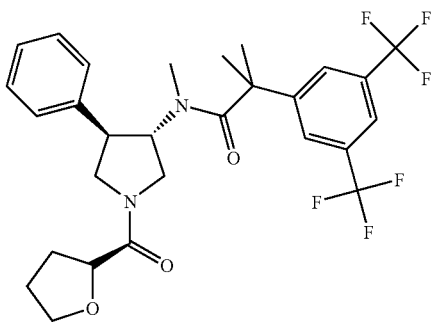

To a stirred solution of (S)-tetrahydro-furan-2-carboxylic acid (described in *J. Med. Chem.*, 1995, 38(15, 2830) (5.0 mg, 0.043 mmol) in THF (2 ml) at RT were added Et$_3$N (12 µl, 0.086 mmol), BOP (25 mg, 0.057 mmol) and rac-2-(3,5-bis-trifluoromethyl-phenyl)-N-methyl-N-((3S,4R)-4-phenyl-pyrrolidin-3-yl)-isobutyramide (Intermediate VII-1) (20 mg, 0.043 mmol). Stirring was continued at 40° C. for 48 hours. Concentration and purification by preparative HPLC afforded 5.1 mg (25%) of the title compound.

ES-MS m/e: 557.2 (M+H$^+$).

Example 58

N-[(3S,4R)-1-((2S,4R)-1-Acetyl-4-hydroxy-pyrrolidine-2-carbonyl)-4-phenyl-pyrrolidin-3-yl]-2-(3,5-bis-trifluoromethyl-phenyl)-N-methyl-isobutyramide

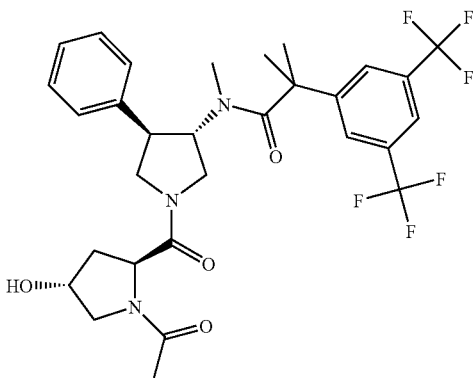

To a stirred solution of (2S,4R)-1-acetyl-4-hydroxy-pyrrolidine-2-carboxylic acid (commercially available) (7.5 mg, 0.043 mmol) in THF (2 ml) at RT were added Et$_3$N (12 µl, 0.086 mmol), BOP (25 mg, 0.057 mmol) and rac-2-(3,5-bis-trifluoromethyl-phenyl)-N-methyl-N-((3S,4R)-4-phenyl-pyrrolidin-3-yl)-isobutyramide (Intermediate VII-1) (20 mg, 0.043 mmol). Stirring was continued at 40° C. for 48 hours. Concentration and purification by preparative HPLC afforded 7.6 mg (29%) of the title compound.

ES-MS m/e: 614.5 (M+H$^+$).

Example 59

2-(3,5-Bis-trifluoromethyl-phenyl)-N-[(3S,4R)-1-(4-methoxymethyl-cyclohexanecarbonyl)-4-phenyl-pyrrolidin-3-yl]-N-methyl-isobutyramide

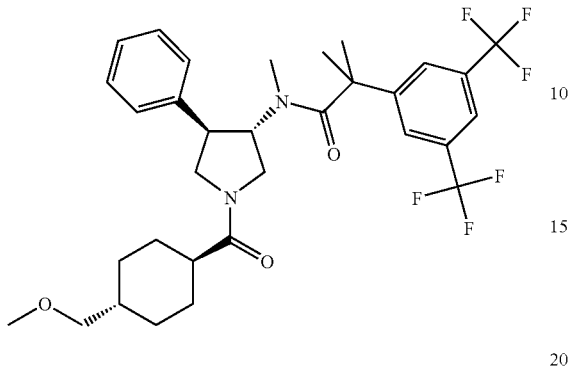

To a stirred solution of 4-methoxymethyl-cyclohexanecarboxylic acid (described in JP60258141) (7.4 mg, 0.043 mmol) in THF (2 ml) at RT were added Et₃N (12 µl, 0.086 mmol), BOP (25 mg, 0.057 mmol) and rac-2-(3,5-bis-trifluoromethyl-phenyl)-N-methyl-N-((3S,4R)-4-phenyl-pyrrolidin-3-yl)-isobutyramide (Intermediate VII-1) (20 mg, 0.043 mmol). Stirring was continued at 40° C. for 48 hours. Concentration and purification by preparative HPLC afforded 12.7 mg (48%) of the title compound.

ES-MS m/e: 613.3 (M+H⁺).

Example 60

2-(3,5-Bis-trifluoromethyl-phenyl)-N-[(3S,4R)-1-(4-ethynyl-cyclohexanecarbonyl)-4-phenyl-pyrrolidin-3-yl]-N-methyl-isobutyramide

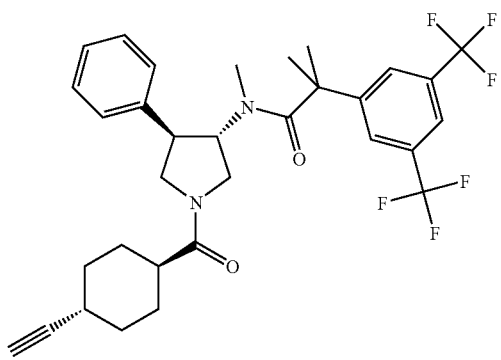

To a stirred solution of 4-ethynyl-cyclohexanecarboxylic acid (commercially available) (6.5 mg, 0.043 mmol) in THF (2 ml) at RT were added Et₃N (12 µl, 0.086 mmol), BOP (25 mg, 0.057 mmol) and rac-2-(3,5-bis-trifluoromethyl-phenyl)-N-methyl-N-((3S,4R)-4-phenyl-pyrrolidin-3-yl)-isobutyramide (Intermediate VII-1) (20 mg, 0.043 mmol). Stirring was continued at 40° C. for 48 hours. Concentration and purification by preparative HPLC afforded 13.7 mg (54%) of the title compound.

ES-MS m/e: 593.5 (M+H⁺).

Example 61 rac-2-[3,5-bis(trifluoromethyl)phenyl]-N-{(3R,4S)-1-[(6'-bromo-2'-oxo-2',3'-dihydro-1H,1'H-spiro[piperidine-4,4'-quinolin]-1-yl)carbonyl]-4-phenylpyrrolidin-3-yl}-N,2-dimethylpropanamide

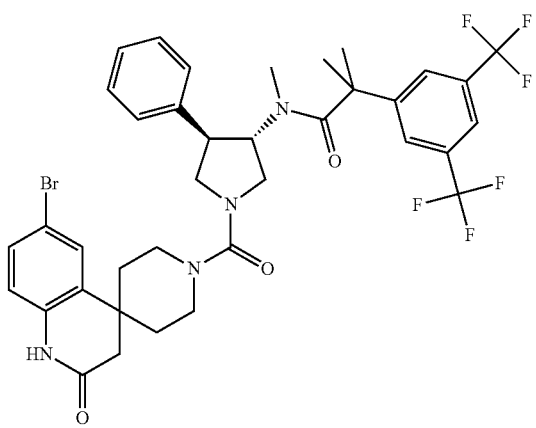

Coupling according to general procedure II:
Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)
Amine: 6'-bromo-1'H-spiro[piperidine-4,4'-quinolin]-2'(3'H)-one
ES-MS m/e: 779.5 (M+H⁺).

Example 62 rac-2-[3,5-bis(trifluoromethyl)phenyl]-N,2-dimethyl-N-{(3R,4S)-1-[(1-oxo-2,3-dihydro-1H,1'H-spiro[isoquinoline-4,4'-piperidin]-1'-yl)carbonyl]-4-phenylpyrrolidin-3-yl}propanamide

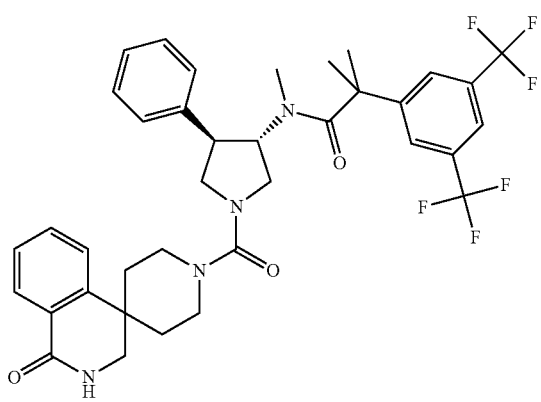

Coupling according to general procedure II:
Pyrrolidine intermediate: rac-(3S,4R)-3-{[2-(3,5-Bis-trifluoromethyl-phenyl)-2-methyl-propionyl]-methyl-amino}-4-phenyl-pyrrolidine-1-carbonyl chloride (VIII-1)
Amine: 2,3-dihydro-1H-spiro[isoquinoline-4,4'-piperidin]-1-one
ES-MS m/e: 701.5 (M+H⁺).

The invention claimed is:
1. A compound of formula I

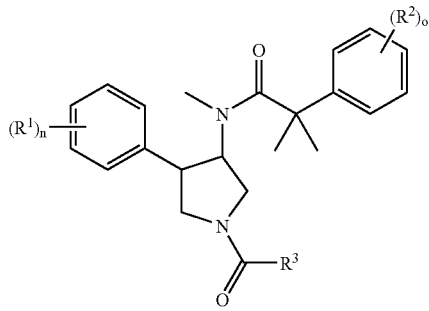

wherein
$R^1$ is hydrogen, halogen or lower alkyl;
$R^2$ is hydrogen, halogen, lower alkoxy or lower alkyl substituted by halogen;
$R^3$ is —$(CH_2)_p$-heterocyclyl optionally substituted by lower alkyl, halogen, —$S(O)_2$-lower alkyl, —C(O)-lower alkyl, —C(O)O-lower alkyl, hydroxy, lower alkyl substituted by hydroxy, —$(CH_2)_p$—O-lower alkyl, or —NHCO-lower alkyl, or is $C_{3-6}$-cycloalkyl optionally substituted by =O, —$(CH_2)_p$—O-lower alkyl or lower alkinyl, or is unsubstituted or substituted aryl or heteroaryl, wherein the substituents are selected from the group consisting of lower alkyl, CN, —$S(O)_2$-lower alkyl, halogen, —C(O)-lower alkyl, hydroxy, lower alkoxy or lower alkoxy substituted by halogen; or is —$(CH_2)_p$—$NR^4R^5$;
$R^4$ and $R^5$ are each independently hydrogen, lower alkyl, —$(CRR')_p$-lower alkyl substituted by hydroxy, —$(CRR')_p$—O-lower alkyl, —$(CRR')_p$—S-lower alkyl, —$(CRR')_p$—O-lower alkyl substituted by hydroxy or $C_{3-6}$-cycloalkyl;
R and R' are each independently hydrogen, lower alkyl or lower alkyl substituted by hydroxyl;
n is 1 or 2;
o is 1 or 2; and
p is 0, 1, 2, 3 or 4;
or a pharmaceutically active acid-addition salt thereof.

2. A compound of claim 1 having formula I-A

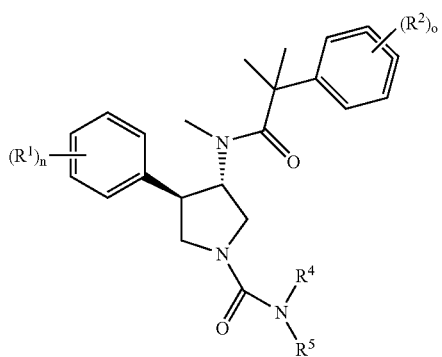

wherein
$R^1$ is hydrogen, halogen or lower alkyl;
$R^2$ is hydrogen, halogen, lower alkoxy or lower alkyl substituted by halogen;

$R^4$ and $R^5$ are each independently hydrogen, lower alkyl, —$(CRR')_p$-lower alkyl substituted by hydroxy, —$(CRR')_p$—O-lower alkyl, —$(CRR')_p$—S-lower alkyl, —$(CRR')_p$—O-lower alkyl substituted by hydroxy or $C_{3-6}$-cycloalkyl;
R and R' are each independently hydrogen, lower alkyl or lower alkyl substituted by hydroxy;
n is 1 or 2;
o is 1 or 2; and
p is 0, 1, 2, 3 or 4;
or a pharmaceutically active acid-addition salt thereof.

3. A compound of claim 2, wherein $R^4$ and $R^5$ are each independently hydrogen or lower alkyl substituted by hydroxy.

4. A compound of claim 3, selected from the group consisting of
rac-(3S,4R)-3-{[2-(3,5-bis-trifluoromethyl-phenyl)-2-methyl-propionyl]-methyl-amino}-4-(4-fluoro-phenyl)-pyrrolidine-1-carboxylic acid bis-(2-hydroxy-ethyl)-amide and
rac-(3S,4R)-3-{[2-(3,5-bis-trifluoromethyl-phenyl)-2-methyl-propionyl]-methyl-amino}-4-(4-fluoro-phenyl)-pyrrolidine-1-carboxylic acid (2-hydroxy-ethyl)-amide.

5. A compound of claim 1 having formula I-B

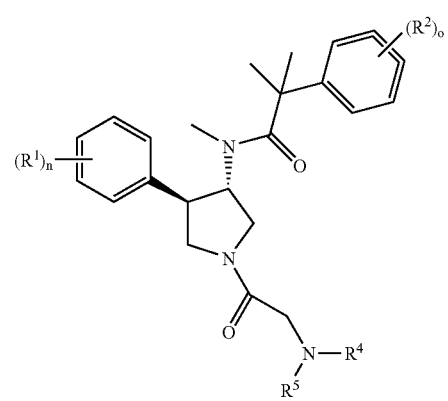

wherein
is hydrogen, halogen or lower alkyl;
$R^1$ is hydrogen, halogen, lower alkoxy or lower alkyl substituted by halogen;
$R^4$ and $R^5$ are each independently hydrogen, lower alkyl, —$(CRR')_p$-lower alkyl substituted by hydroxy, —$(CRR')_p$—O-lower alkyl, —$(CRR')_p$—S-lower alkyl, —$(CRR')_p$—O-lower alkyl substituted by hydroxy or $C_{3-6}$-cycloalkyl;
R and R' are each independently hydrogen, lower alkyl or lower alkyl substituted by hydroxy;
n is 1 or 2;
o is 1 or 2; and
p is 0, 1, 2, 3 or 4;
or a pharmaceutically active acid-addition salt thereof.

6. A compound of claim 1 having formula I-C

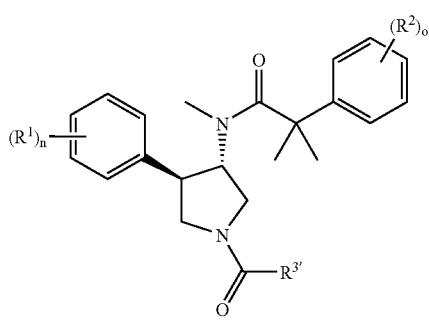

wherein
- $R^1$ is hydrogen, halogen or lower alkyl;
- $R^2$ is hydrogen, halogen, lower alkoxy or lower alkyl substituted by halogen;
- $R^3$ is —$(CH_2)_p$-heterocyclyl optionally substituted by lower alkyl, halogen, —$S(O)_2$-lower alkyl, —C(O)-lower alkyl, —C(O)O-lower alkyl, hydroxy, lower alkyl substituted by hydroxy, —$(CH_2)_p$—O-lower alkyl or —NHCO-lower alkyl;
- n is 1 or 2;
- o is 1 or 2; and
- p is 0, 1, 2, 3 or 4;

or a pharmaceutically active acid-addition salt thereof.

7. A compound of claim 1, wherein the substituent $(R^2)_o$ is 3,5-di-$CF_3$.

8. A compound of claim 7, wherein $R^3$ is morpholinyl.

9. A compound of claim 8, selected from the group consisting of
- rac-2-(3,5-bis-trifluoromethyl-phenyl)-N-[(3S,4R)-4-(4-chloro-phenyl)-1-(morpholine-4-carbonyl)-pyrrolidin-3-yl]-N-methyl-isobutyramide,
- rac-2-(3,5-dichloro-phenyl)-N-[(3S,4R)-4-(4-fluoro-phenyl)-1-(morpholine-4-carbonyl)-pyrrolidin-3-yl]-N-methyl-isobutyramide and
- rac-2-(3,5-bis-trifluoromethyl-phenyl)-N-[(3S,4R)-4-(4-fluoro-2-methyl-phenyl)-1-(morpholine-4-carbonyl)-pyrrolidin-3-yl]-N-methyl-isobutyramide.

10. A compound of claim 7, wherein $R^3$ is piperazinyl, substituted by $S(O)_2$-lower alkyl or C(O)-lower alkyl.

11. A compound of claim 8, selected from the group consisting of
- rac-2-(3,5-bis-trifluoromethyl-phenyl)-N-[(3S,4R)-4-(4-fluoro-phenyl)-1-(4-methanesulfonyl-piperazine-1-carbonyl)-pyrrolidin-3-yl]-N-methyl-isobutyramide,
- rac-N-[(3S,4R)-1-(4-acetyl-piperazine-1-carbonyl)-4-(4-fluoro-phenyl)-pyrrolidin-3-yl]-2-(3,5-bis-trifluoromethyl-phenyl)-N-methyl-isobutyramide,
- rac-2-(3,5-bis-trifluoromethyl-phenyl)-N-[(3S,4R)-1-(4-methanesulfonyl-piperazine-1-carbonyl)-4-phenyl-pyrrolidin-3-yl]-N-methyl-isobutyramide,
- rac-2-(3,5-dichloro-phenyl)-N-[(3S,4R)-4-(4-fluoro-phenyl)-1-(4-methanesulfonyl-piperazine-1-carbonyl)-pyrrolidin-3-yl]-N-methyl-isobutyramide,
- rac-2-(3,5-bis-trifluoromethyl-phenyl)-N-[(3S,4R)-4-(4-fluoro-2-methyl-phenyl)-1-(4-methanesulfonyl-piperazine-1-carbonyl)-pyrrolidin-3-yl]-N-methyl-isobutyramide and
- rac-N-[(3S,4R)-4-(4-chloro-phenyl)-1-(4-methanesulfonyl-piperazine-1-carbonyl)-pyrrolidin-3-yl]-2-(3,5-dichloro-phenyl)-N-methyl-isobutyramide.

12. A pharmaceutical composition comprising a therapeutically effective amount of a compound of formula I

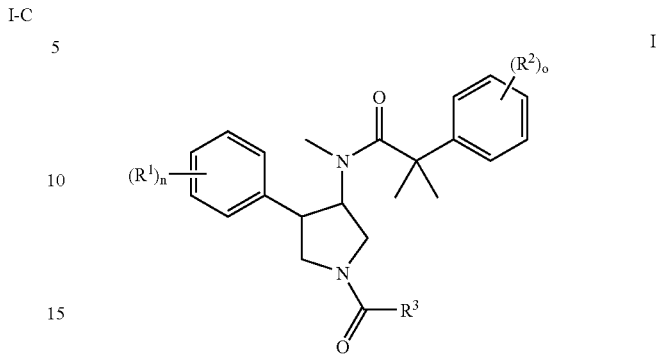

wherein
- $R^1$ is hydrogen, halogen or lower alkyl;
- $R^2$ is hydrogen, halogen, lower alkoxy or lower alkyl substituted by halogen;
- $R^3$ is —$(CH_2)_p$-heterocyclyl optionally substituted by lower alkyl, halogen, —$S(O)_2$-lower alkyl, —C(O)-lower alkyl, —C(O)O-lower alkyl, hydroxy, lower alkyl substituted by hydroxy, —$(CH_2)_p$—O-lower alkyl, or —NHCO-lower alkyl, or is $C_{3-6}$-cycloalkyl optionally substituted by =O, —$(CH_2)_p$—O-lower alkyl or lower alkinyl, or is unsubstituted or substituted aryl or heteroaryl, wherein the substituents are selected from the group consisting of lower alkyl, CN, —$S(O)_2$-lower alkyl, halogen, —C(O)-lower alkyl, hydroxy, lower alkoxy or lower alkoxy substituted by halogen; or is —$(CH_2)_p$—$NR^4R^5$;
- $R^4$ and $R^5$ are each independently hydrogen, lower alkyl, —$(CRR')_p$-lower alkyl substituted by hydroxy, —$(CRR')_p$—O-lower alkyl, —$(CRR')_p$—S-lower alkyl, —$(CRR')_p$—O-lower alkyl substituted by hydroxy or $C_{3-6}$-cycloalkyl;
- R and R' are each independently hydrogen, lower alkyl or lower alkyl substituted by hydroxyl;
- n is 1 or 2;
- o is 1 or 2; and
- p is 0, 1, 2, 3 or 4;

or a pharmaceutically active acid-addition salt thereof and a pharmaceutically acceptable carrier.

13. The composition of claim 12, wherein the compound of formula I have formula I-A

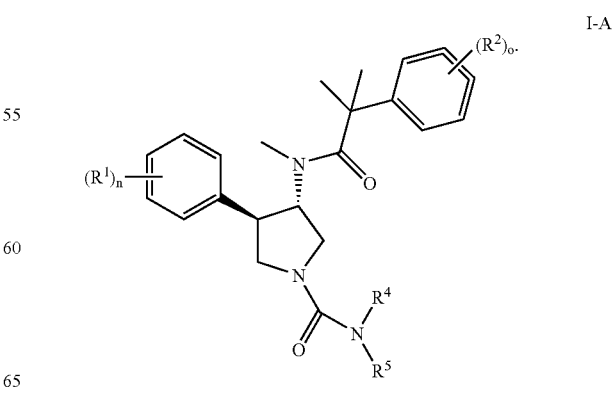

14. The composition of claim 12, wherein the compound of formula I have formula I-B
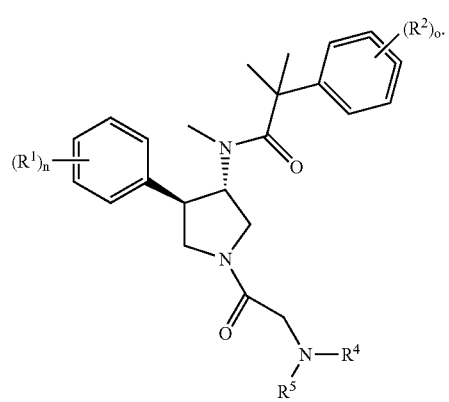
15. The composition of claim 12, wherein the compound of formula I have formula I-C
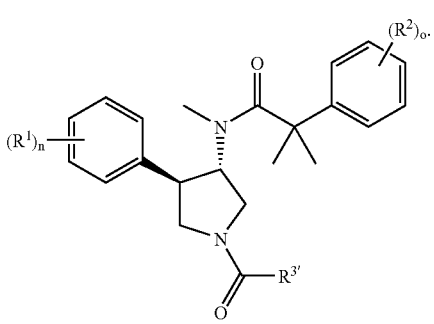
* * * * *